(12) United States Patent
Ferguson et al.

(10) Patent No.: US 7,558,619 B2
(45) Date of Patent: Jul. 7, 2009

(54) RAMAN INSTRUMENT FOR MEASURING WEAK SIGNALS IN THE PRESENCE OF STRONG BACKGROUND FLUORESCENCE

(75) Inventors: Scott Ferguson, Spanish Fork, UT (US); John F. Fralick, Salt Lake City, UT (US); Scott Douglas Bergeson, Orem, UT (US); Justin Peatross, Provo, UT (US)

(73) Assignee: Nu Skin International, Inc., Provo, UT (US)

( * ) Notice: Subject to any disclaimer, the term of this patent is extended or adjusted under 35 U.S.C. 154(b) by 327 days.

(21) Appl. No.: 11/244,434

(22) Filed: Oct. 4, 2005

(65) Prior Publication Data

US 2007/0078349 A1 Apr. 5, 2007

(51) Int. Cl.
*A61B 5/00* (2006.01)
(52) U.S. Cl. .................... 600/476; 600/473
(58) Field of Classification Search ................ 600/310, 600/473, 475–477
See application file for complete search history.

(56) References Cited

U.S. PATENT DOCUMENTS

| | | | |
|---|---|---|---|
| 4,832,483 A | 5/1989 | Verma | |
| 5,206,699 A | 4/1993 | Stewart et al. | |
| 5,697,373 A | 12/1997 | Richards-Kortum et al. | |
| 5,873,831 A | 2/1999 | Bernstein et al. | |
| 6,044,285 A | 3/2000 | Chaiken et al. | |
| 6,069,689 A | 5/2000 | Zeng et al. | |
| 6,151,522 A * | 11/2000 | Alfano et al. | 600/473 |
| 6,205,354 B1 | 3/2001 | Gellermann et al. | |
| 6,208,887 B1 | 3/2001 | Clarke | |
| 6,281,971 B1 | 8/2001 | Allen et al. | |
| 6,289,230 B1 | 9/2001 | Chaiken et al. | |
| 6,352,502 B1 | 3/2002 | Chaiken et al. | |
| 6,377,828 B1 | 4/2002 | Chaiken et al. | |

(Continued)

OTHER PUBLICATIONS

Shreve, A.P. et al., "Effective Rejection of Fluorescence Interference in Raman Spectroscopy Using A Shifted Excitation Difference Technique", *Applied Spectroscopy*, The Society For Applied Spectroscopy. Baltimore, U.S., vol. 46, No. 4, Apr. 1, 1992, pp. 707-711, XP000264023, ISSN: 0003-7028.

(Continued)

*Primary Examiner*—Brian Casler
*Assistant Examiner*—Peter Luong
(74) *Attorney, Agent, or Firm*—Stuart R. Hemphill; Dorsey & Whitney LLP

(57) ABSTRACT

A method for measuring a chemical concentration in tissue has two measurement steps. A portion of tissue is illuminated with a first generated light and a second generated light. A first Raman scattered light, corresponding to the first generated light, and a second Raman scattered light, corresponding to the second generated light, are directed to a plurality of light sensors, each light sensor measuring light at a different wavelength, that wavelength being proximate to a wavelength of an expected Raman shift wavelength for the chemical in the tissue. A measurement is obtained from each light sensor, each measurement being specific to the first scattered light and/or the second reflected light to that light sensor. The measurements of the first scattered light and the measurements of the second scattered light are used to calculate a concentration of the chemical in the tissue.

33 Claims, 20 Drawing Sheets

U.S. PATENT DOCUMENTS

| | | | |
|---|---|---|---|
| 6,426,045 | B1 | 7/2002 | Jeng et al. |
| 6,503,478 | B2 | 1/2003 | Chaiken et al. |
| 6,681,133 | B2 | 1/2004 | Chaiken et al. |
| 6,721,582 | B2 | 4/2004 | Trepagnier et al. |
| 6,961,599 | B2 * | 11/2005 | Lambert et al. ............. 600/318 |
| 2004/0260183 | A1 * | 12/2004 | Lambert et al. ............. 600/476 |
| 2006/0197947 | A1 | 9/2006 | Wang et al. |

OTHER PUBLICATIONS

Wesley R. Browne, et al. "The Raman effect and its application to electronic spectroscopies in metal-centered species: Techniques and investigations in ground and excited states", ScienceDirect/Coordination Chemistry Reviews, vol. 251, 2007, pp. 454-473.

Nerine J. Cherepy et al., "Near Infrared Resonance Spectroscopy of the Special Pair and the Accessory *Bacteriochlorophylls* Reaction Centers", J. Phys, Chem. 1994, 98, 6023-6029.

* cited by examiner

RAMAN INSTRUMENT FOR MEASURING WEAK SIGNALS IN THE PRESENCE OF STRONG BACKGROUND FLUORESCENCE

FIELD OF THE INVENTION

The present invention relates a method and apparatus for measuring levels of chemical compounds found in biological tissue. More specifically, the invention relates to a method and apparatus for the noninvasive detection and measurement of levels of carotenoids or other selected molecules in biological tissue.

BACKGROUND OF THE INVENTION

Carotenoids are plant pigments available from the diet that may have important effects in the human body. For example, it is thought that many carotenoids seem to have positive effects on immune function, which can be critical in stopping cancer. Carotenoids also have an antioxidant effect which may protect against heart disease. Further, some studies have shown that carotenoids may help reduce the risk of degenerative diseases, such as age-related macular degeneration.

Recently, researchers have focused on the carotenoids alpha-carotene (in carrots), lycopene (in red fruits and vegetables, such as tomatoes and red peppers), beta cryptoxanthin (in oranges), and lutein and zeaxanthin (in broccoli and leafy green vegetables). Some research shows people with deficiencies of these substances are more likely to develop certain kinds of cancer, particularly lung cancer, supporting the theory that increased consumption of these carotenoids might protect against cancer and that identification of a deficiencies of these substances may alert an individual to possible health concerns. One study particularly looked at lutein, a carotenoid found in many vegetables and fruits, including spinach, broccoli, lettuce, tomatoes, oranges, carrots, celery, and greens. The study evaluated nearly 2,000 people with colon cancer and found that lutein intake in the study group was considerably lower than it was in people who were cancer-free.

It has been demonstrated that carotenoids offer some degree of biologic protection against the formation of malignancies in various tissues. For example, carotenoids have been shown in animal models to prevent carcinoma formation in tissues such as skin, salivary gland, mammary gland, liver, and colon. In addition, low levels of carotenoids and related substances such as retinoids have been assessed as high risk factors for malignant lesions. For example, having low levels of the carotenoid lycopene has been associated with prostate and cervical cancer; the carotenoids lutein, zeaxanthin, alpha-carotene, and beta-carotene with lung cancer; and beta-carotene with oral cancer. Therefore, quantitatively measuring the chemical concentrations of these carotenoids, retinoids and other related substances provides an indicator of the risk or presence of cancer.

Skin cancer is the most common cancer in the United States. Methods to provide detection of the levels of chemicals which are associated with skin related malignancies are of great assistance to physicians and medical personnel in the early diagnosis and treatment of skin cancer.

It has been theorized that carotenoids in the skin provide biologic protection from cutaneous malignancy. Prior methods used to detect the presence of chemicals associated with skin cancer have mainly been through the analysis of tissues obtained by biopsies or other invasive procedures. A standard method presently used for measuring carotenoids is through high-performance liquid chromatography (HPLC) techniques. Such techniques require removal of large amounts of tissue sample from the patient for subsequent analysis and processing, which typically takes at least twenty-four hours to complete. Thus, this technique is both invasive and slow and also expensive.

A noninvasive method for the measurement of carotenoid levels in the macular tissue of the eye is described in U.S. Pat. No. 5,873,831, in which levels of carotenoids and related substances are measured using Raman spectroscopy. Raman spectroscopy can identify the presence and concentration (provided proper calibration is performed) of certain chemical compounds. Nearly monochromatic light is incident upon the sample to be measured, and the inelastically scattered light, which is of a different wavelength than the incident light, is detected and measured. The wavelength shift between the incident and scattered light is known as the Raman shift, and the shift corresponds to an energy which is the "fingerprint" of the vibrational or rotational energy state of certain molecules. Typically, a molecule exhibits several characteristic Raman active vibrational or rotational energy states, and the measurement of the molecule's Raman spectrum thus provides a fingerprint of the molecule, i.e., it provides a molecule-specific series of spectrally sharp vibration or rotation peaks. The intensity of the Raman scattered light corresponds directly to the concentration of the molecule(s) of interest.

One difficulty associated with Raman spectroscopy is the very low signal intensity which is inherent to Raman scattered light. It is well known that the scattered light intensity scales with the wavelength raised to the fourth power. The weak Raman signal must be distinguished from Rayleigh scattered light, which is elastically scattered light of the same wavelength as the incident light and which constitutes a much greater fraction of the total scattered light. The Raman signal can be separated from Rayleigh scattered light through the use of filters, gratings, or other wavelength separation devices; however, this can have the effect of further weakening the measured Raman signal through the additional attenuation that can occur when the light passes through a wavelength separation device. In practice, the Raman scattered light is extremely difficult to detect. One might attempt to increase the Raman signal by increasing the intensity of the incident light on the tissue sample. Lasers have been used as a light source to increase light intensity, but this can cause burning or degradation of the sample.

In order to overcome some of these difficulties, a technique known as resonance Raman spectroscopy has been used, as described in U.S. Pat. No. 5,873,831, referenced hereinabove. Such a technique is also described in U.S. Pat. No. 4,832,483. In resonance Raman spectroscopy, the incident illumination utilized has a wavelength which corresponds to the resonance wavelength corresponding to electron energy transitions of the molecules of interest. This has the effect of strongly enhancing the Raman output signal without using a higher intensity input signal, thereby avoiding damage to the sample which can be caused by laser burning. Also, these resonance Raman signals have much higher intensity than off-resonance Raman signals, which are virtually invisible at power levels that will not damage human tissue. Therefore, in resonance Raman spectroscopy only those Raman signals which belong to the species of interest are obtained.

In the above referenced U.S. Pat. No. 5,873,831, the resonance Raman technique is used to measure the levels of the carotenoids lutein and zeaxanthin, two chemicals which are associated with healthy macular tissue of the human eye. The above referenced U.S. Pat. No. 4,832,483 uses resonance Raman spectroscopy to measure certain carotenoids in blood plasma, and suggests the use of the ratios of the intensities of the Raman spectral peaks as a method of indicating the presence of various malignancy diseases.

Yet another difficulty associated with Raman measurements is that the substances of interest in the skin not only scatter incident light, but can absorb and subsequently fluoresce with substantial intensity. This fluorescence often comprises a very strong, spectrally broad signal that tends to "drown out" or overwhelm the Raman spectral peaks, increasing the difficulty of identification and quantification of the substances.

Fluorescence spectroscopy is itself another technique that can be used to measure amounts of chemical compounds in biological tissue. For example, U.S. Pat. No. 5,697,373 discloses use of fluorescence and/or Raman spectroscopy to detect tissue abnormality in the cervix. The disadvantage of fluorescence measurements is that since many different molecules fluoresce in broad bands of wavelengths, such measurements cannot be used to identify conclusively the presence or concentration of a particular substance.

U.S. Pat. No. 6,205,354 shows a system that uses a laser to excite tissue such as an area of skin on the hand and measure carotenoid levels through an observation of the spectrum of the resulting scattered light. The faint but narrowband Raman peak must be distinguished from the broadband fluorescence background in the spectrum (typically over 100 times brighter). The system in U.S. Pat. No. 6,205,354 uses a technique that estimates the level of fluorescence (or background light) underneath the Raman peak by doing a curve fit to portions of the spectrum adjacent to either side of the expected Raman peak, but not part of the peak. The spectral resolution necessary for this analysis severely limits the amount of light that can be collected from the tissue with a standard spectrometer, which the system relies on. It requires that the excited tissue area to be small, just a fraction of a millimeter. Lasers are a good source of monochromatic light that can be focused to a small spot for the Raman excitation, but lasers with wavelengths in the needed blue-green spectral region are expensive and somewhat difficult to keep stable in environments with varying physical conditions. Moreover, estimating the level of background light beneath the Raman peak based on measurements of light to either side of the peak is susceptible to error that can vary with specific hardware variability.

It would therefore be a significant advance to provide an apparatus and method to measure chemical concentrations in tissue using Raman spectroscopy which has sufficient spectral measurement sensitivity to accommodate a relatively large tissue excitation area and which does not require the use of a laser or a baseline estimate of fluorescence levels beneath the Raman peak. Such an apparatus would make more widely available safe, noninvasive, rapid, accurate, and specific measurement of the levels of carotenoids and other similar chemical compounds that are present in varying degrees in biological tissues.

BRIEF SUMMARY OF THE INVENTION

A method for measuring a chemical concentration in tissue has two measurement steps. First, generating a first light and illuminating a portion of the tissue with the first light; capturing a first reflected light from the tissue; directing the first reflected light to a plurality of light sensors, each light sensor measuring light at a different wavelength, that wavelength being proximate to a wavelength of an expected Raman shift wavelength for the chemical in the tissue; and obtaining a measurement from each of the light sensors, each measurement being specific to the first reflected light through that light sensor. Second, generating a second light and illuminating a portion of the tissue with the second light; capturing a second reflected light from the tissue; directing the second reflected light to the plurality of light sensors, each light sensor measuring light at a different wavelength that wavelength being proximate to a wavelength of an expected Raman shift wavelength for the chemical in the tissue; and obtaining a measurement from each of the light sensors, each measurement being specific to the second reflected light through that light sensor. The measurements of the first reflected light and the measurements of the second reflected light are used to calculate a concentration of the chemical in the tissue.

While multiple embodiments are disclosed, still other embodiments of the invention will become apparent to those skilled in the art from the following detailed description, which shows and describes illustrative embodiments of the invention. As will be realized, the invention is capable of modifications in various obvious aspects, all without departing from the spirit and scope of the invention. Accordingly, the drawings and detailed description are to be regarded as illustrative in nature and not restrictive.

DETAILED DESCRIPTION OF THE INVENTION

Figure 1:
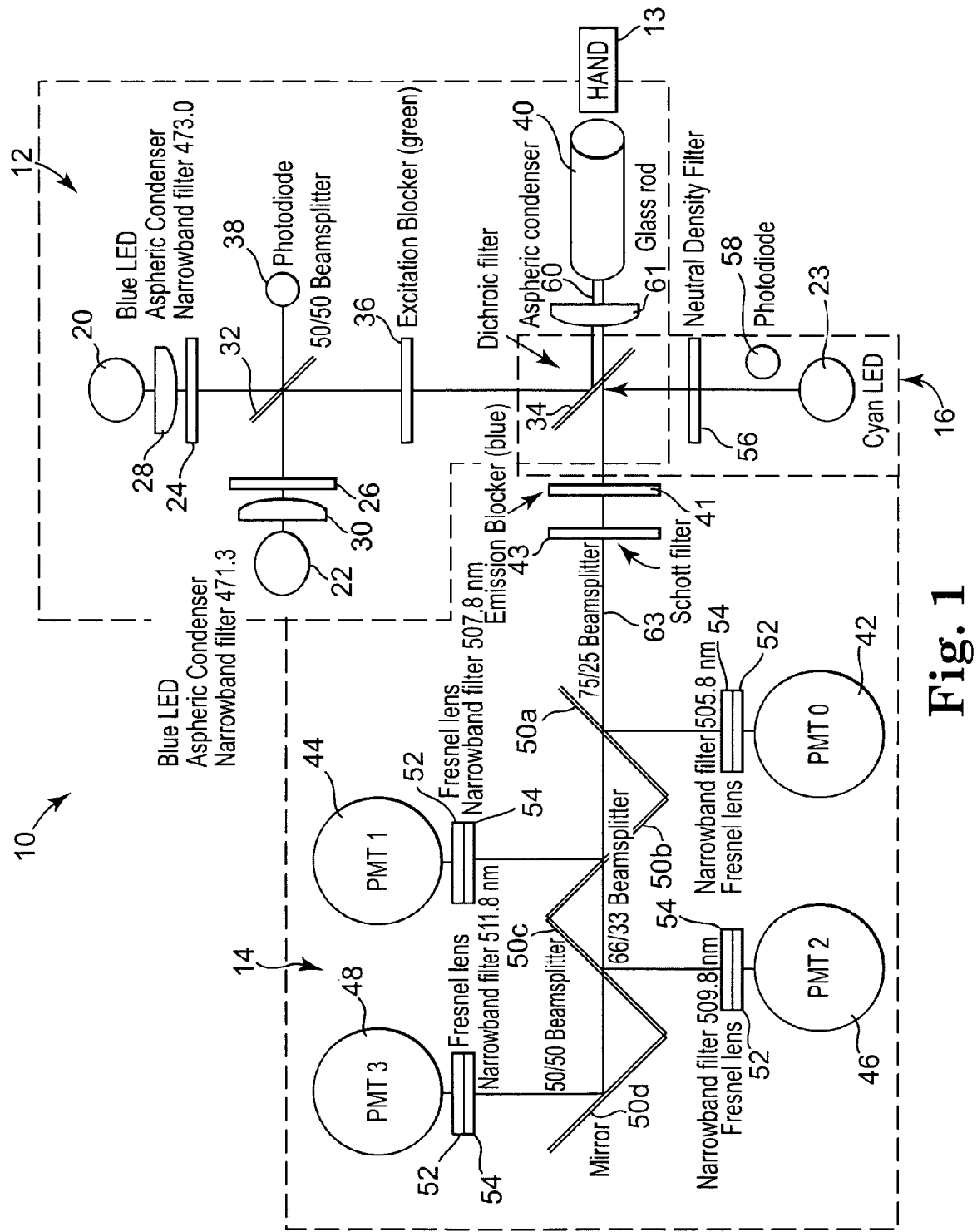
FIG. 1 is a schematic diagram of the basic light handling components of the apparatus.

A method and apparatus for the measurement of the levels of carotenoids and other related substances or other selected molecules in biological tissue or a target sample, such as living skin is provided. The apparatus comprises an excitation portion, an analyzer portion, and a calibration portion. The apparatus enables noninvasive, rapid, safe, and accurate determination of the levels of carotenoids (including their isomers and metabolites) and similar substances in tissue. This information can be a marker for conditions where carotenoids or other antioxidant compounds may provide useful information.

Examples of biological tissues which can be measured non-invasively with the technique of the invention include human skin on a hand. It is anticipated that measurements may also be made for cervix, colon, and lungs. With the addition of appropriate sample presentation accessories, it is expected that bodily fluids that can be measured will include saliva, whole blood, and mucus.

Overview of Method

The method and apparatus use resonance Raman spectroscopy, which is used to identify and quantify the presence of carotenoids and similar substances or other selected molecules in biological tissue, such as the skin. Monochromatic or nearly monochromatic excitation light (for example, from a light emitting diode) is directed onto tissue or other target and the scattered light is then spectrally filtered and detected. This process is based on the premise that certain molecular structures in a target, when excited by light at a characteristic wavelength impinging on the target, will emit light at a different, specific wavelength. The intensity of the inelastically scattered photons emitted by the molecular structure, the Raman emissions, is a function of wavelength separation, or Raman shift, from the wavelength of a monochromatic excitation source. For example, when exposed to light at 473.0 nanometers, the carbon to carbon conjugated double bonds in carotenoids will emit light at 509.8 nanometers.

As will be described more fully below, nearly monochromatic excitation light at approximately 473.0 nanometers may be directed at the target. Scattered light is emitted from the target and includes both Rayleigh and Raman scattered light and also fluorescence from the target. The Rayleigh light is light that is elastically scattered (or scattered at the same wavelength as the incident excitation light).

A portion of the small remainder of the light that is scattered in an inelastic fashion, and is therefore of different wavelengths than the incident excitation light, forms the Raman signal. When the light source excites carotenoids with light at 473.0 nanometers, the carotenoids emit a Raman signal centered at 509.8 nanometers, and its intensity correlates to the amount of carotenoids in the tissue. The Rayleigh and the Raman scattered light are separated in wavelength. Much of the excitation light is also absorbed at the target and leads to fluorescence emission from the target. The difficulty in the Raman measurement is the removal of this obscuring non-Raman fluorescence component near 509.8 nanometers, which is typically 100 times stronger than the Raman signal. Analysis of the Raman signal comprises removing the background light (fluorescence and Rayleigh emissions) from the measurement.

The wavelength difference between the excitation light and the Raman scattered light is known as the Raman shift and is typically measured as a difference in wave numbers or wavelengths, and can be converted into a corresponding wavelength shift. The Raman shift is independent of the wavelength of incident light used. Thus, for example, when the excitation wavelength is 473.0 nanometers, the Raman peak for carotenoid molecules occurs at 509.8 nanometers, whereas when the excitation wavelength is 471.3 nanometers, the Raman peak occurs at 507.8 nanometers. The amount of shift from the wavelength of the excitation light is an indication of the type of molecule present, and the intensity of a Raman peak corresponds directly to the concentration of the molecule present that caused the shift. As alluded to previously, specific wave number shifts correspond to certain vibrational or rotational modes of these chemical structures. Thus, while the method and apparatus is discussed in relation to a light source providing excitation light at approximately 471.3 nanometers and 473.0 nanometers, a wide range of excitation wavelengths work approximately equally well with a corresponding wavelength shift.

As discussed above, Raman spectroscopy in tissues using short visible wavelengths is complicated due to very high native fluorescence, particularly in skin tissue, which masks the weaker Raman signals. To distinguish the Raman signal from background fluorescence (which is at least 50 and typically 100 times brighter than Raman signals), two measurements are made that enable the removal of the background fluorescence. In the first measurement, the tissue is briefly exposed to an excitation wavelength at 473.0 nanometers. In the second measurement, the tissue is exposed to blue light at 471.3 nanometers. The exact separation between these two wavelengths is not critical, just as the exact wavelength values are not critical. Thus, other wavelengths and/or other separations between wavelengths may be used. Generally, it is preferable to have the two excitation wavelengths be close together or adjacent but sufficiently far apart that they do not merge on account of the bandwidth of filters (including, for example, excitation bandpass filters and PMT bandpass filters, both discussed below). In a specific embodiment discussed herein, the excitation filters are 1.7 nanometers apart with filter widths of 0.8 nanometers. This puts the Raman peaks corresponding to the two excitation wavelengths at 2 nanometers apart, with some broadening due to the bandwidth of the excitation filters. The bandpass filters in front of the PMTs designed to observe the Raman light have bandwidths of 1 nanometer, which effectively introduces further broadening of the peaks. The wavelength separation is desirably as tight as possible within the constraints of the bandwidth of the filters. Further, if desired, the filter separation may be wider, for example, 3 nanometers.

The light emitted from the tissue exhibits similar levels of fluorescence in both the first and the second measurements because the variation in light directed at the tissue is relatively small. The emitted light at several wavelengths near and including the Raman signal peak, for example, 505.8 nanometers, 507.8 nanometers, 509.8 nanometers, and 511.8 nanometers, is measured for each excitation wavelength, 473.0 nanometers and 471.3 nanometers. That is, four samples of emissions are taken with a wavelength range of about 505 nanometers to about 512 nanometers. Accordingly, in some embodiments, the sampled emitted intensity values thus may cover a wavelength range of less than 10 nanometers or of less than 7 nanometers. The wavelength range and the specific sampling wavelengths are chosen to include a value at or near the characteristic emission wavelength Fc associated with the selected molecule and each excitation wavelength, at least one sample adjacent the characteristic wavelength Fc but sufficiently displaced below that wavelength to exclude Raman emissions resulting from the illumination for such excitation wavelength and at least one sample adjacent the characteristic wavelength Fc but sufficiently displaced above that wavelength to exclude Raman emissions resulting from the illumination for such excitation wavelength. These measurements may then be used to calculate the concentration of carotenoids (the chemical associated with this Raman shift) in the tissue. More specifically, the measurements of individual wavelengths emitted from the tissue for the two excitation wavelengths are then divided into themselves. Because the measurements are nearly identical for the two excitation wavelengths, the ratio is close to 1 for each wavelength observed near the Raman signal peak wavelength. In this manner, the strong fluorescence background as well as variability in detector response are removed by the division. However, since the Raman peak due to carotenoids occurs at a different wavelength for the two excitation wavelengths, it does not divide away. Thus, using the method and apparatus, carotenoid levels may be determined even in the presence of the strong native fluorescence.

Overview of Apparatus

The apparatus generates light at wavelengths that produce a Raman response with a wavelength shift that is characteristic of carotenoids. The apparatus has components allowing it to perform measurements of emitted light resulting from two excitation wavelengths, typically selected between approximately 470 and 475 nanometers, and directs the light onto the tissue or other target, but other wavelengths may also be used. The elastically and inelastically scattered light and fluorescence from the tissue is collected, with the inelastically scattered light having characteristic energy shifts and quantifiable intensities which produce a Raman signal corresponding to carotenoids in the tissue. The intensity of the inelastically scattered light forming the Raman signal is quantified through analysis of the two measurements.

Light Handling Components

FIG. 1 schematically illustrates the components of apparatus 10. The apparatus 10 comprises an excitation portion 12, an analyzer portion 14, and a calibration portion 16. The excitation portion 12 generates light to which the tissue or other target is exposed. The analyzer portion 14 receives the light that returns from the target and measures the amount of light at specific wavelengths. The calibration portion 16 gathers data that may be used to analyze raw data and compute the final measure of quantities of carotenoids. A computer (not shown in FIG. 1) is used to control the apparatus 10 and perform the analysis. Calculations of the final carotenoid level value may be performed on the computer after it receives all the raw data or in processors that are resident in the apparatus that help gather the raw data. In the latter case, a small amount of analyzed data and results may be communicated to the computer for display or storage. Location of the data analysis is not significant to the methodology.

The excitation portion 12 comprises two light sources 20, 22. The light sources 20, 22 may comprise, for example, light emitting diodes (LEDs). In one embodiment the LEDs 20, 22 are similar and emit light at a range of wavelengths that encompasses the wavelength range 470-475 nanometers. To obtain two different and specific wavelengths, the light from each of the light sources 20, 22 is passed through an associated aspheric collimating lens 28, 30 and narrowband optical filter 24, 26. The collimating lens and optical filter are merely example optical components and focusing structures, and others or none may be used so long as the light reaching the target has the desired qualities. Thus, for example, the light from the first light source 20 is passed through a 473.0 nanometer, narrowband optical filter 24. The light from the second light source 22 is passed through a 471.3 nanometer, narrowband optical filter 26. It should be understood, however, that the present invention is not limited to light generated within these wavelengths. Nor do the light sources need to be LEDs; they could be, for example, lasers made to emit at two separate wavelengths.

The collimated light from the first light source 20 strikes and proceeds through a beamsplitter 32, while the collimated light from the second light source 22 strikes the opposite side and reflects from the same beamsplitter 32. In the embodiment shown, the beamsplitter is a 50:50 beamsplitter. This puts the light from the two light sources onto a common path at the expense of half the light. The beamsplitter 32 operates only to establish the light path and direct the light from light sources 20, 22 to the target and need not be provided in embodiments where the light is directed to the tissue by other means, such as light fibers or a single light source with two narrowband filters that are moved into and out of the collimated light path. The light then proceeds through an excitation blocker 36 which is used to more completely eliminate light from the sources with wavelengths in the neighborhood of the Raman signal to be generated. The excitation blocker blocks wavelengths other than those at the wavelength of interest. More specifically, the excitation blocker may block wavelengths that are to be collected from the tissue. Thus, for example, if the reflected light from the tissue is to comprise cyan light, cyan light is blocked by the excitation blocker. The photodiode 38 is used to monitor the intensity of the light sources, observing the light wasted by the 50:50 beamsplitter 32, and can be incorporated in the calibration process to correct for intensity variations in the light sources that may occur. The light originating from either light source 20, 22 then is reflected by a dichroic beamsplitter 34 designed to be highly reflective for light at the excitation wavelengths but highly transmitting for wavelengths near the expected Raman peak to be generated.

Figure 2:
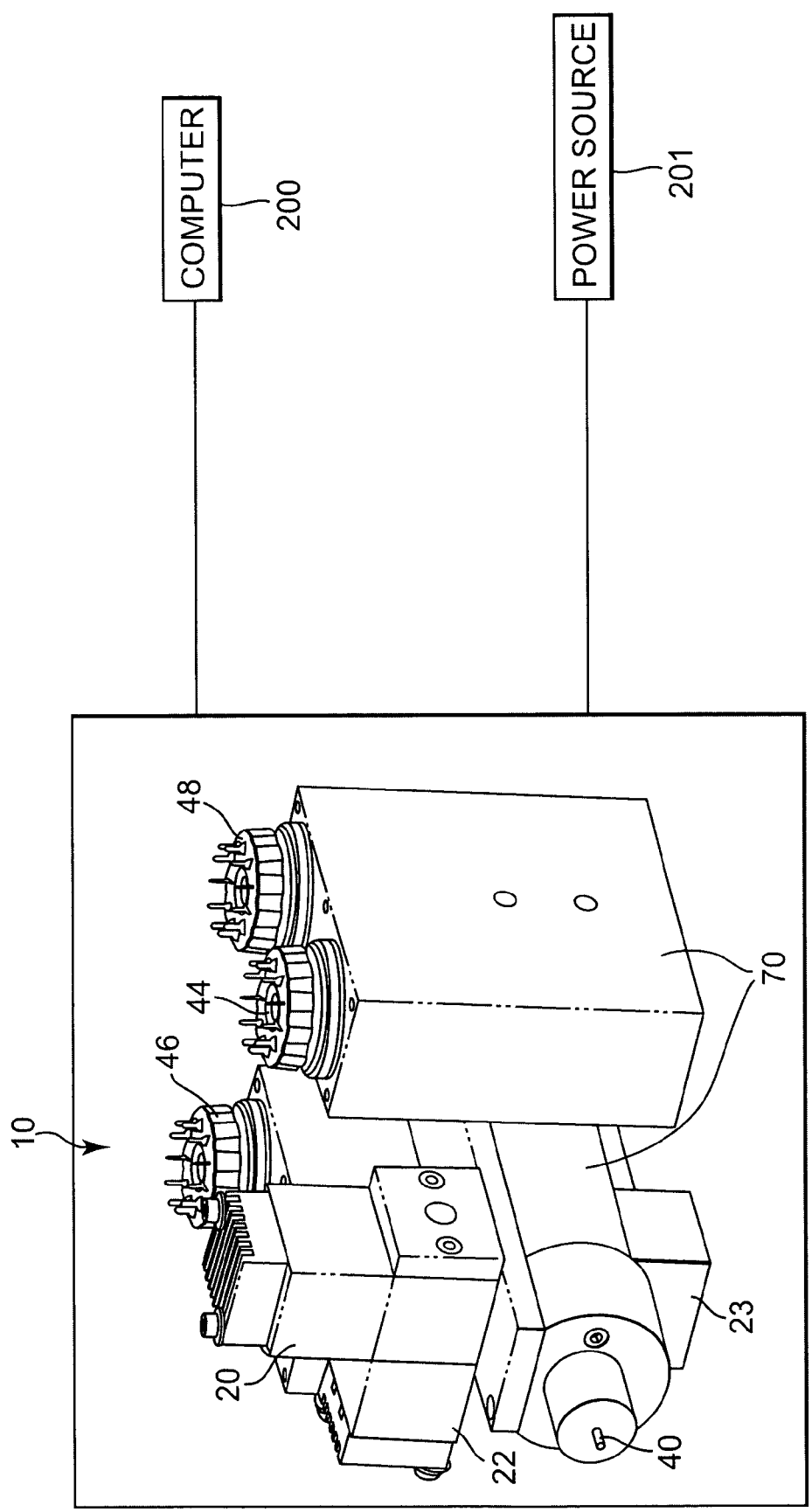
FIG. 2 is a pictorial view from the front and schematic diagram of the apparatus, its control computer and its power source.
Figure 3:
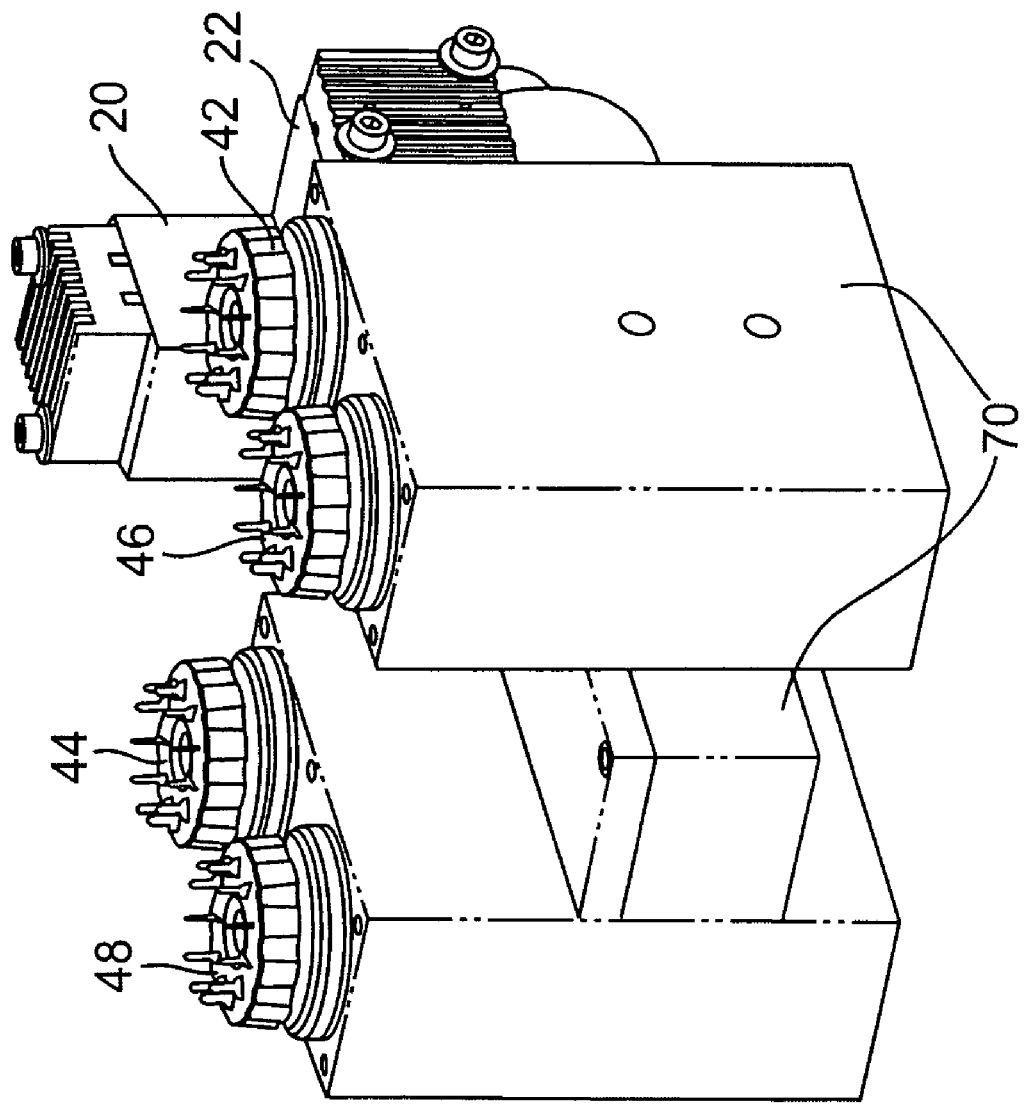
FIG. 3 is a pictorial view from the rear of the internal housings for the main components of the spectrometer.
Figure 4:
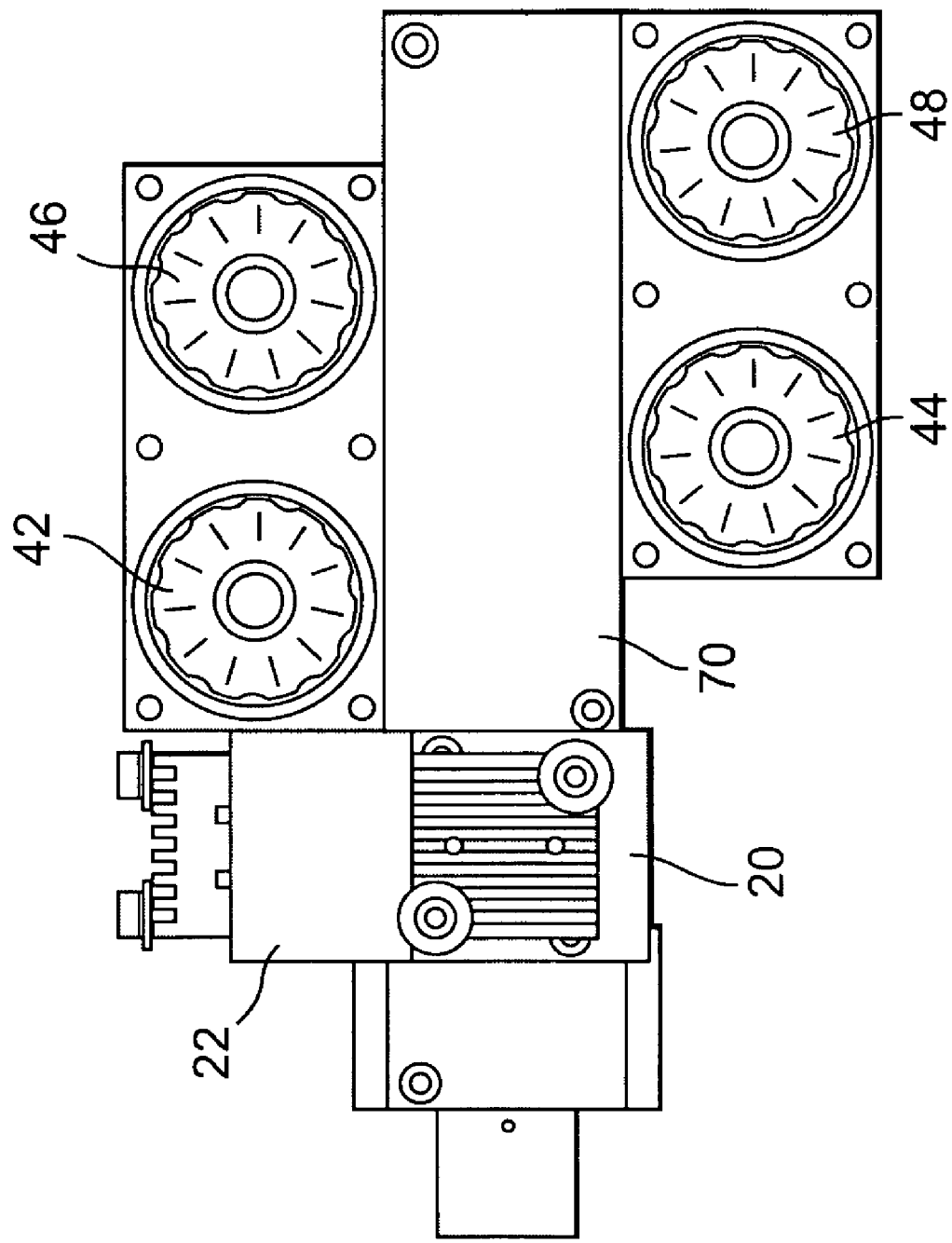
FIG. 4 is a top view of the internal housings for the main components of the apparatus.
Figure 5:
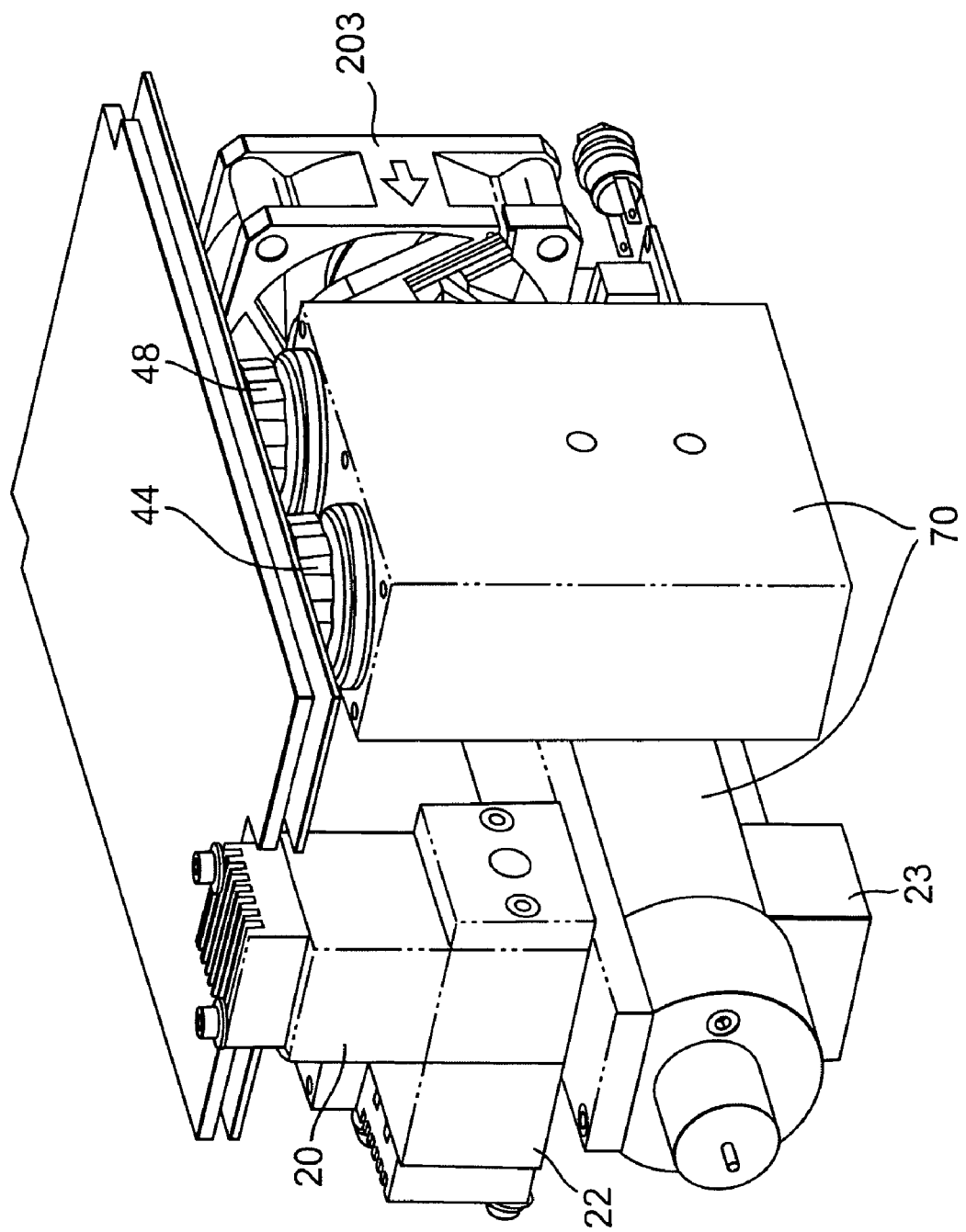
FIG. 5 is a pictorial view from the front of the internal housings for the main components of the apparatus and also showing the location of upper circuit boards for support components and the cooling fan.
Figure 6:
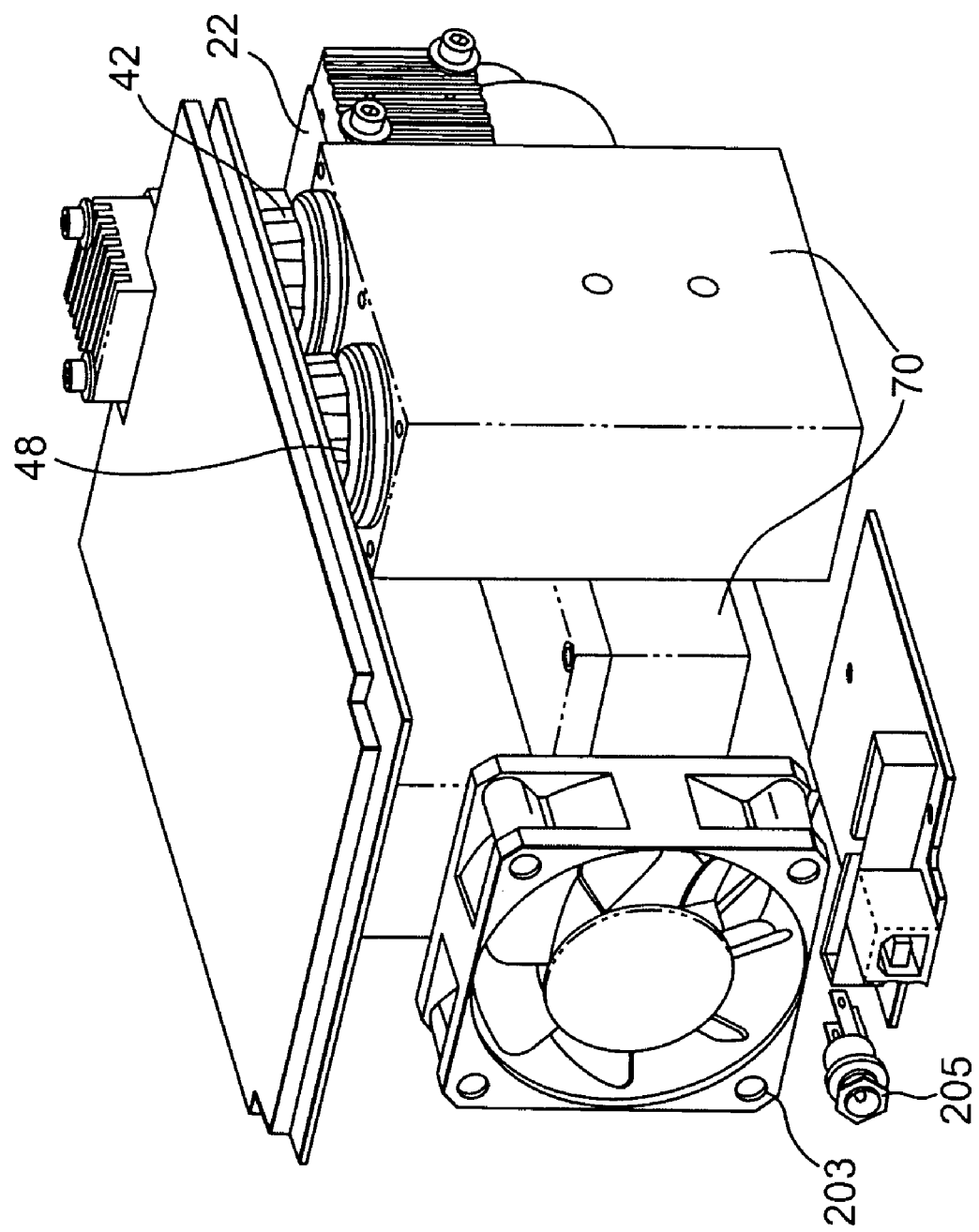
FIG. 6 is pictorial view from the rear of the internal housings for the main components of the apparatus and also showing the location of lower circuit board for support components and the cooling fan.
Figure 7:
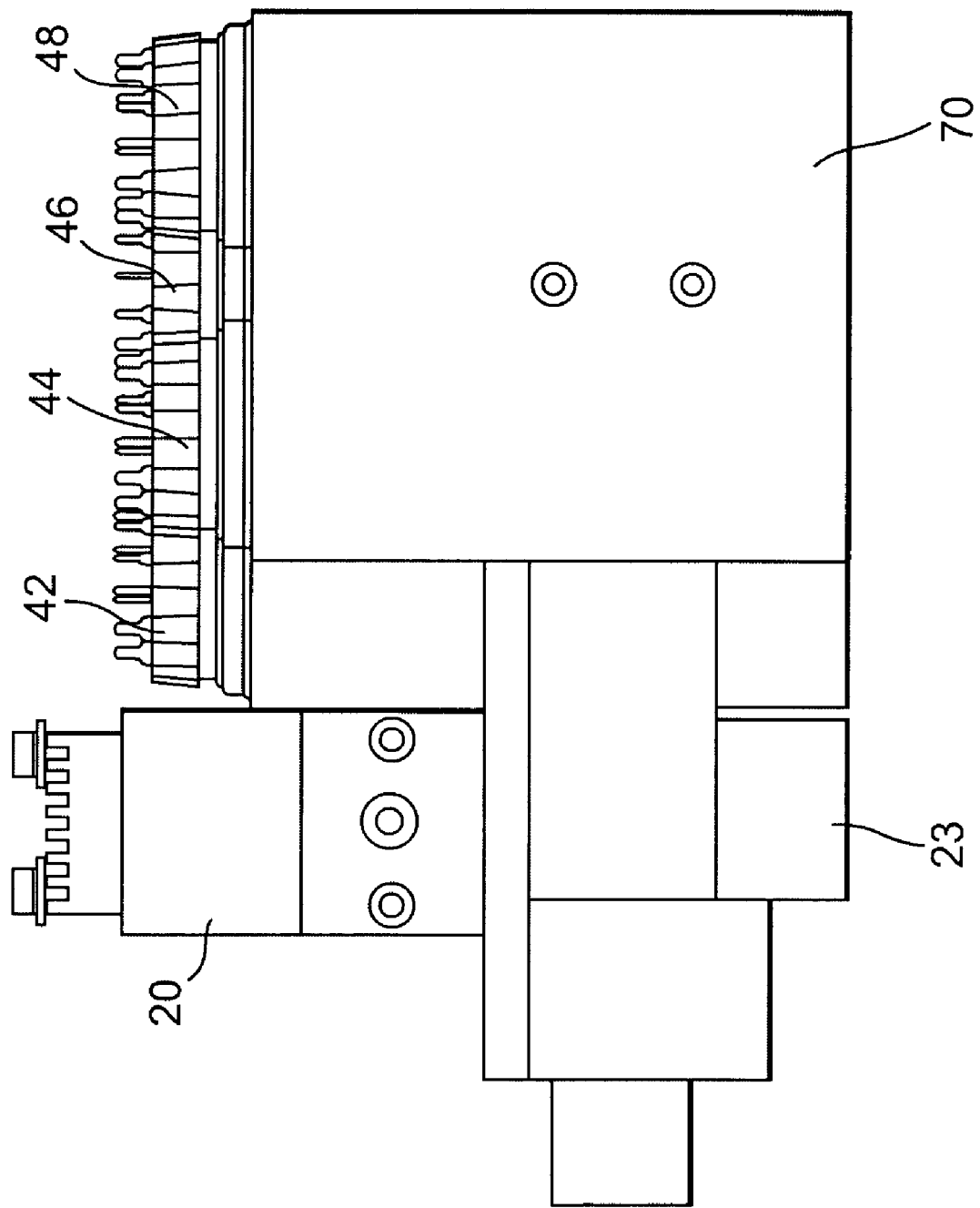
FIG. 7 is a left side view of the internal housings for the main components of the apparatus.
Figure 8:
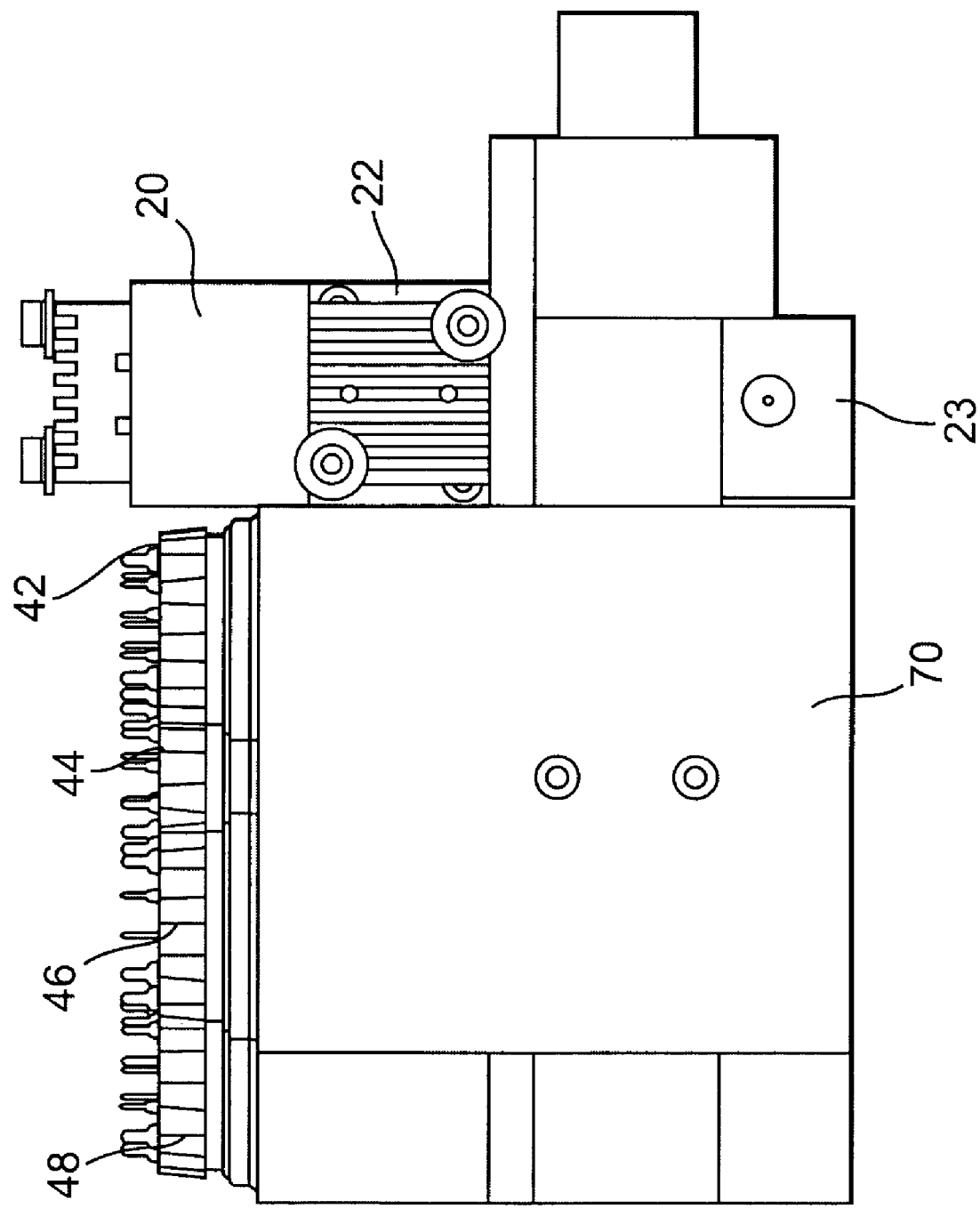
FIG. 8 is a right side view of the internal housings for the main components of the apparatus.
Figure 9:
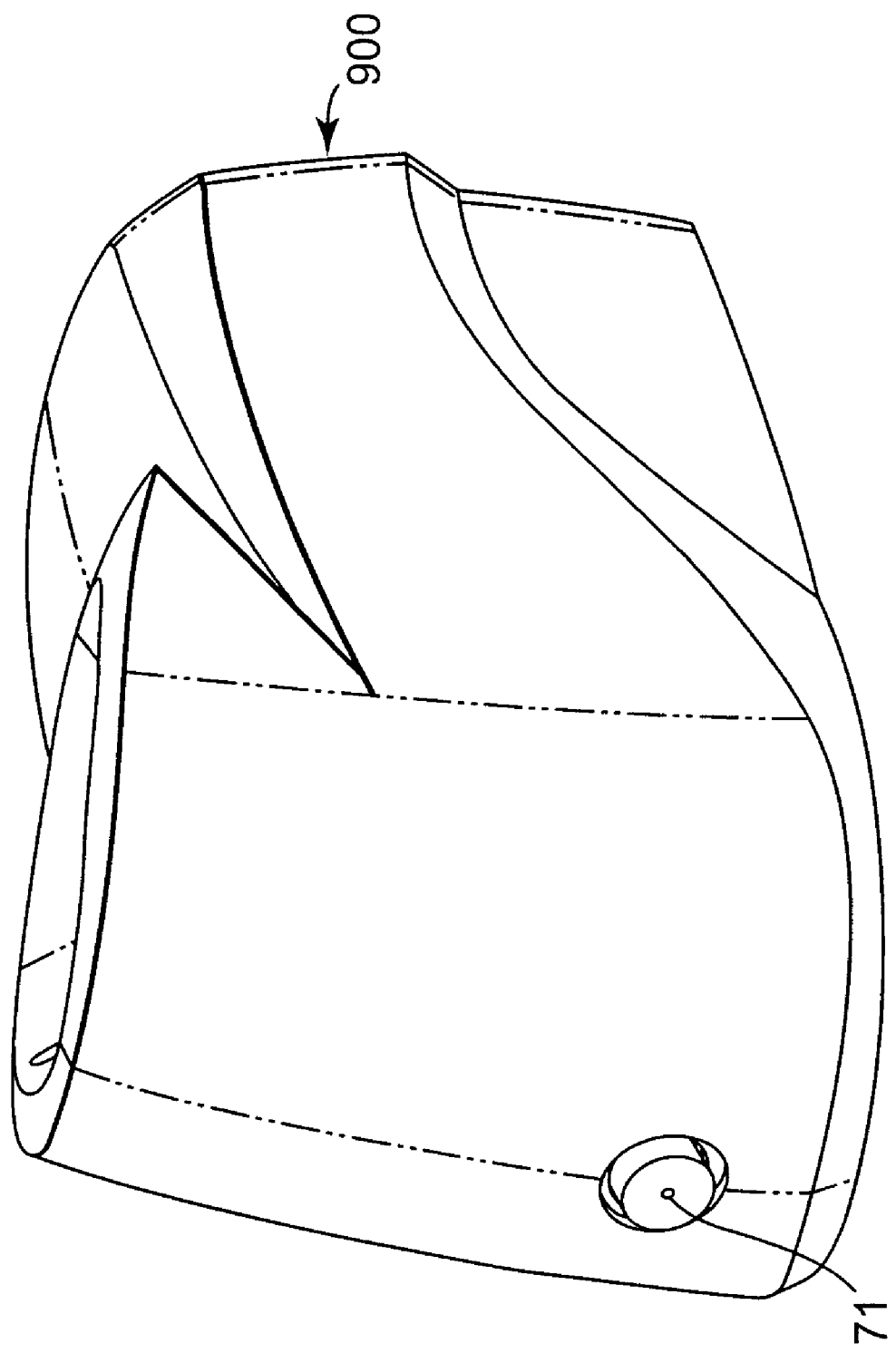
FIG. 9 is a pictorial view from the front of the exterior of the apparatus.
Figure 10:
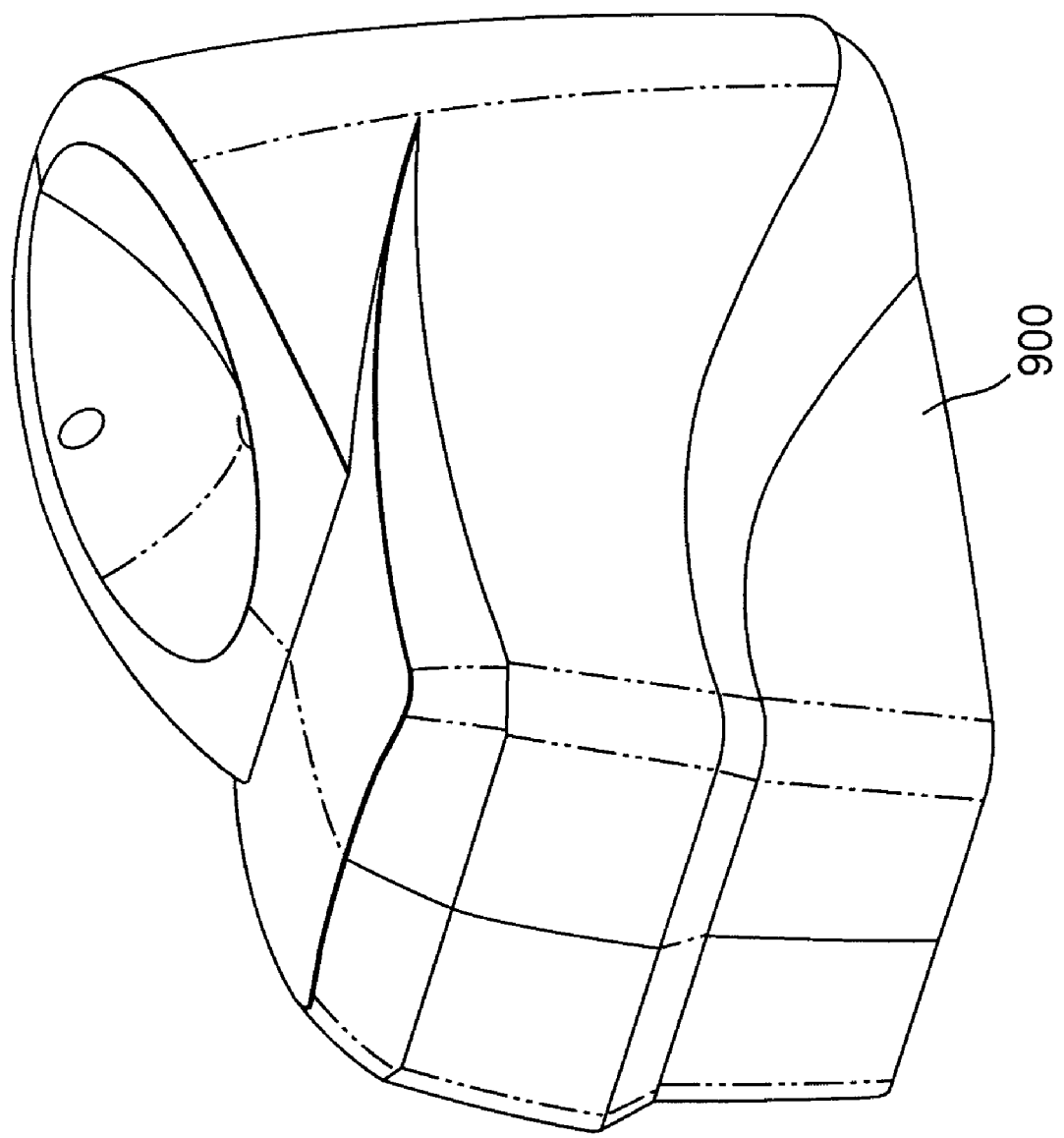
FIG. 10 is a pictorial view from the rear of the exterior of the apparatus.
Figure 11:
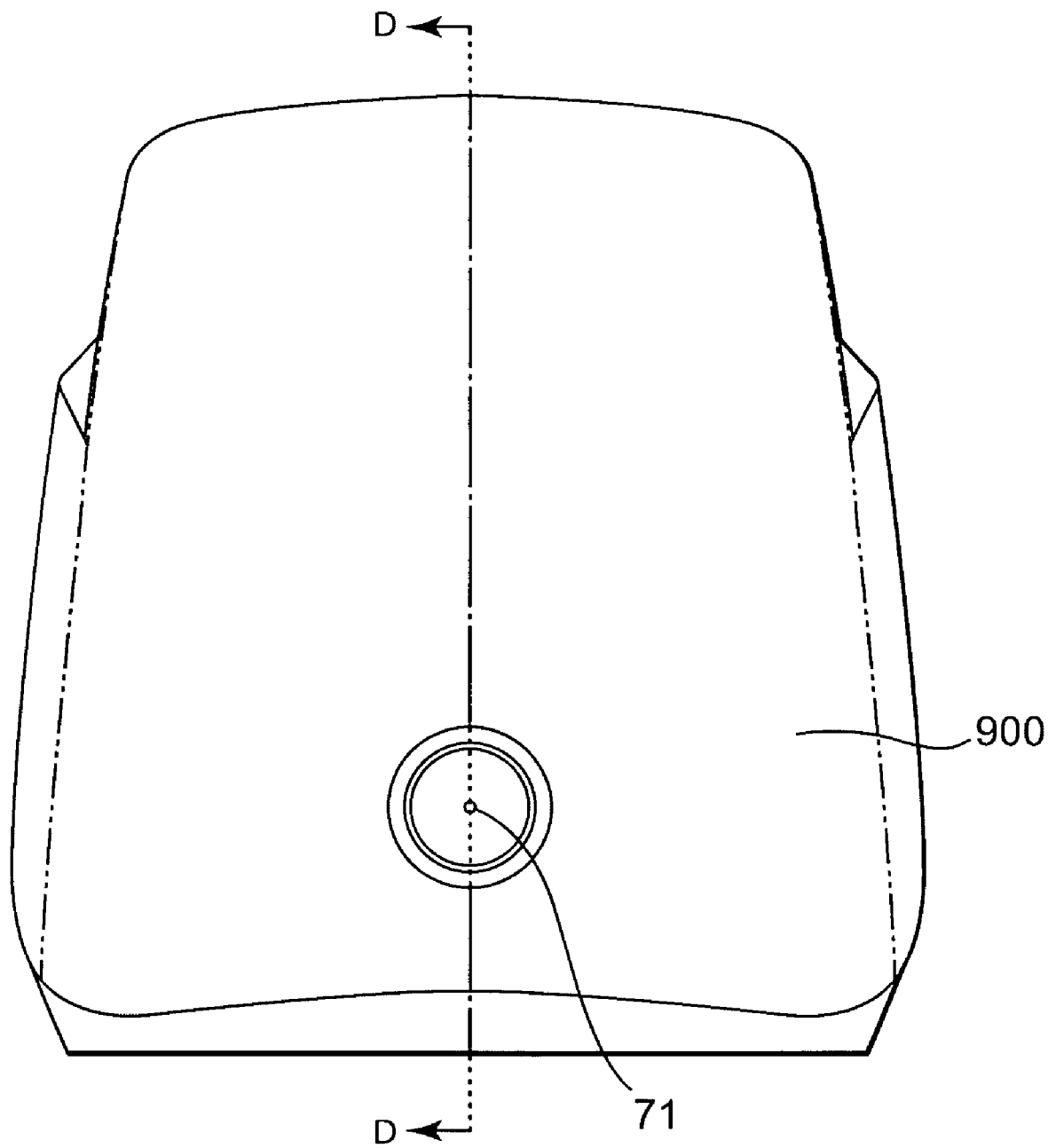
FIG. 11 is a rear view of the exterior of the apparatus.
Figure 12:
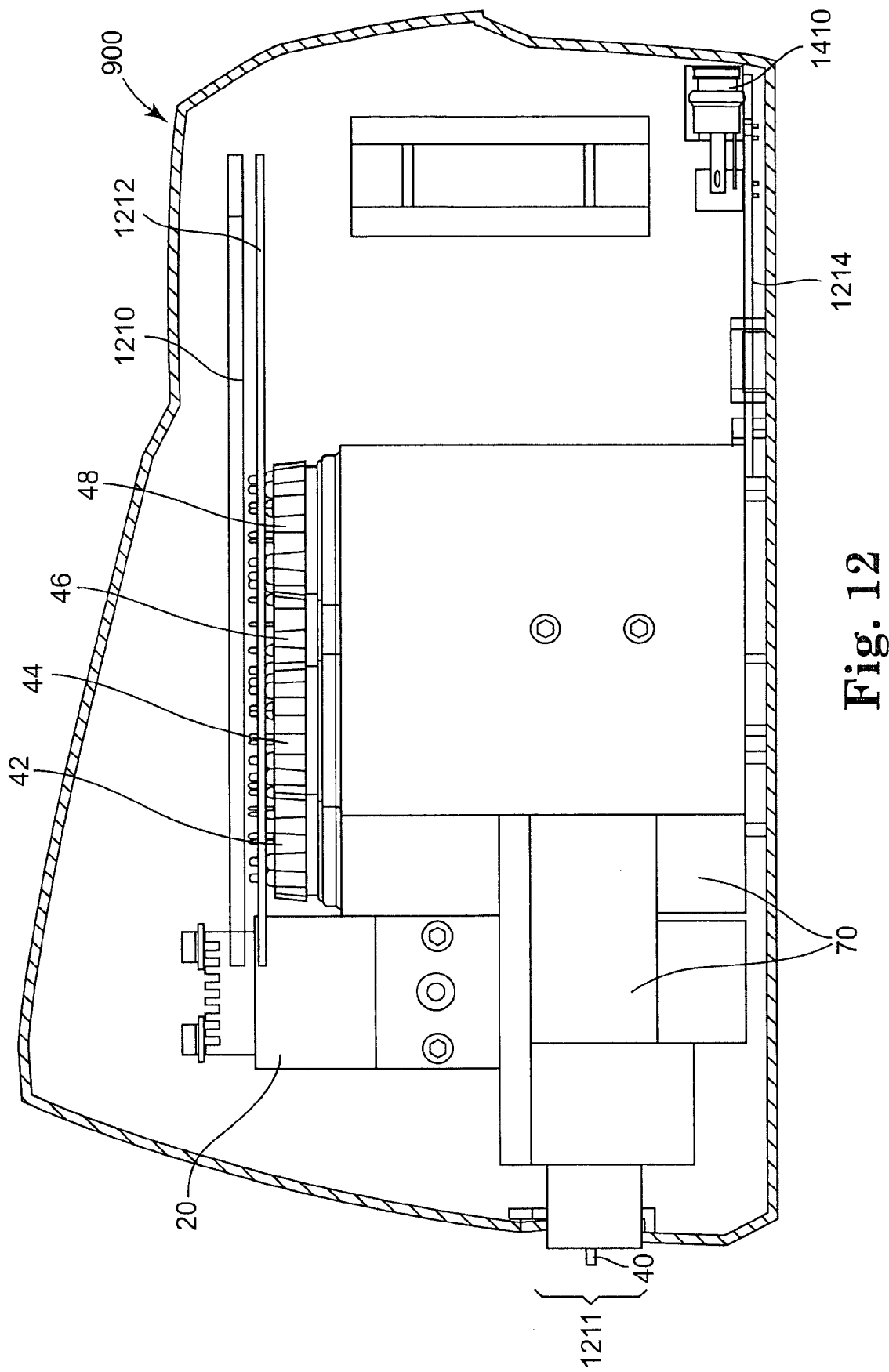
FIG. 12 is a pictorial and cross-sectional view from the left side of the interior of the apparatus.
Figure 13:
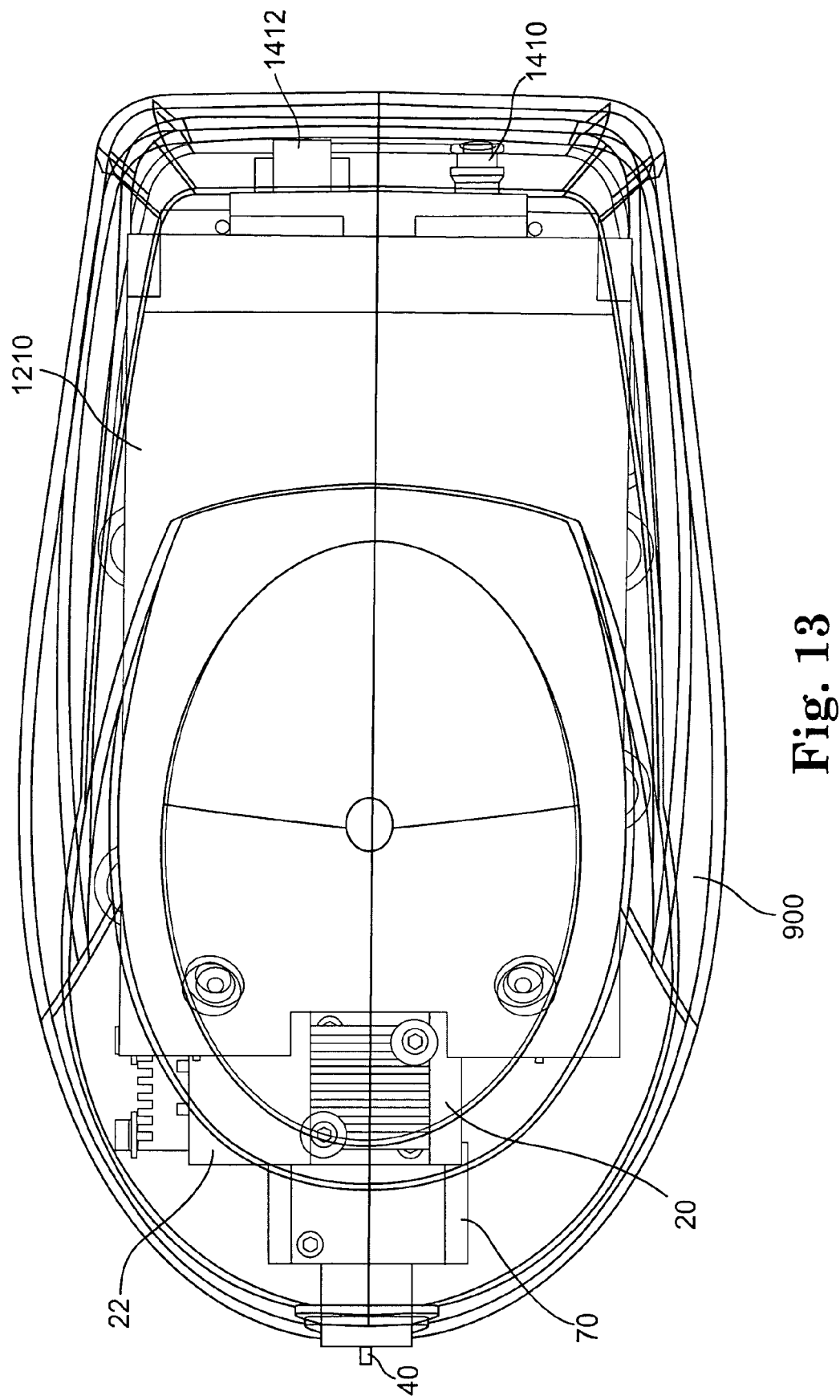
FIG. 13 is a pictorial and internal view from the top of the interior of the apparatus.
Figure 14:
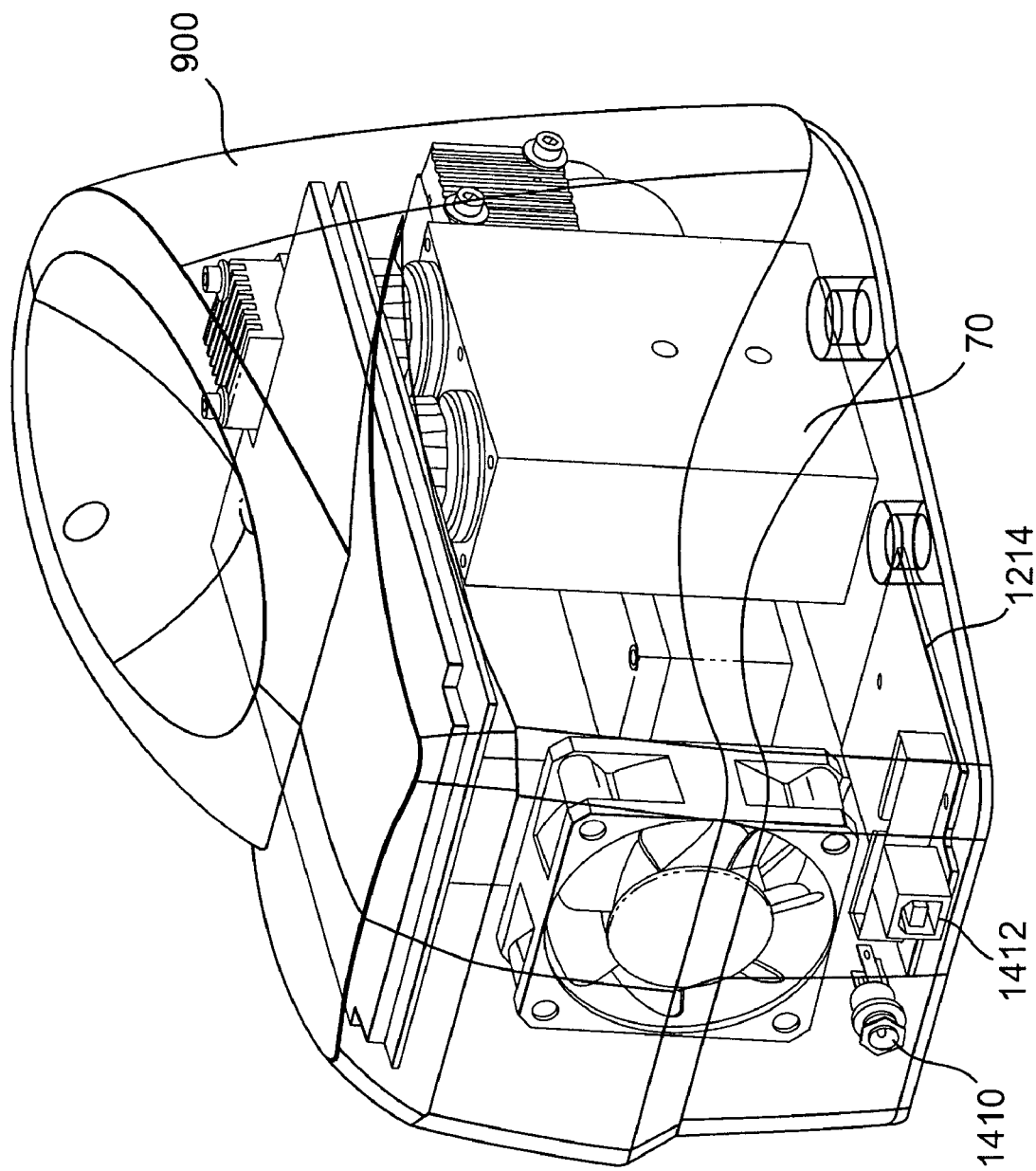
FIG. 14 is a pictorial and internal view from a rear angle of the interior of the apparatus.

The excitation light reflected by the dichroic beamsplitter 34 travels along the axis 60 and is focused by an aspheric condensor lens 61 onto the end of a light conducting rod 40 that serves as a beam homogenizer before the light reaches the tissue. This removes influences from variations in the light sources and optical filters which otherwise could corrupt the measurements. The rod 40 directs the light to and into the tissue and illuminates a spot on the tissue. In one embodiment, the rod 40 is a glass rod that illuminates a spot of approximately two millimeters diameter. As can be seen with reference to FIGS. 2 and 12, the rod 40 may extend slightly past an opening 71 of the apparatus 10 to ensure that the rod 40 contacts the tissue or target 13. The tissue or target 13 may be, for example, a hand, as shown in FIG. 1.

Components in the optical path (for example, the aspheric condensers 28, 30 and the rod 40) may have an anti-reflective coating to reduce reflections at their surfaces.

The emitted light returning from the tissue travels back on a central optical axis 63 through the rod 40 and through the aspheric condensor and the dichroic beamsplitter 34 to the analyzer portion 14. (While axis 63 for returning light is shown separate from central axis 60 in FIG. 1, this is for explanation only; the axes 60, 63 actually coincide.) An emission blocker 41 limits the spectral content of the light to span the wavelengths used in the analyzer portion 14 of the apparatus 10. In the embodiment shown, the light passes through the emission blocker 41, which reduces the Rayleigh-scattered light at the excitation wavelength. The light may then be directed through a color-glass filter 43. The color-glass filter is a spectral blocker and may be provided to absorb Rayleigh scattered light. The passband of the color-glass filter is sufficiently broad to transmit the wavelength to be measured by the analyzer portions sensors. The analyzer portion 14 directs the light to a light detection system capable of measuring the intensity of the emitted light at several wavelengths in the range of interest, such as the wavelengths characteristic of carotenoids in the skin. In the embodiment shown, the light detection system is comprised of a plurality of separate high-sensitivity photodetectors such as photomultiplier tubes that detect and measure light, which is converted into sampled intensity values stored for further processing. Other high-sensitivity devices such as avalanche photo-diodes, a CCD (Charge Coupled Device) detector array, or intensified CCD detector array may be employed, if they have sufficient gain and low noise levels.

In the embodiment shown, the light detection system comprises four photomultiplier tubes (PMTs) 42, 44, 46, 48. The light is partitioned and directed in approximately equal amounts to each PMT. PMTs are light detectors that are useful in low-intensity applications such as fluorescence spectroscopy. Due to high internal gain, PMTs have the ability to measure low levels of light with high sensitivity. Photomultiplier tubes generally comprise a photocathode and a series of dynodes in an evacuated glass enclosure. Photons that strike the photoemissive cathode emit electrons due to the photoelectric effect. The electrons are accelerated through the dynode chain and a cascading effect generates $10^5$ to $10^7$ electrons for each photon hitting the first cathode.

A beam splitter is provided associated with each PMT (PMT0-PMT3 in FIG. 1) such that the light directed along the central axis 63 is split equally among the PMTs 42, 44, 46, 48. Thus, in the embodiment shown, four beam splitters 50a-50d are provided. An analyzer filter 54 and a focusing lens 52 are provided in the optical path from each of the beam splitters 50a-50d to each of the PMTs 42, 44, 46, 48. The focusing lens 52 may be a fresnel lens that focuses the light onto the active area of the PMT. Each filter 54 is a band pass filter that only passes light at a specific wavelength. The first beam splitter 50a diverts one quarter of the light to PMT0 42. The second beam splitter 50b diverts one third of the remaining light to provide one fourth of the total emitted light to PMT1 44. The third beam splitter 50c diverts one half of the remaining light to provide one fourth of the total emitted light to PMT2 46. The fourth beam splitter 50d, namely a mirror, diverts all of the remaining light to provide one fourth of the total emitted light to PMT3 48. In this way, the PMTs 42, 44, 46, 48 can each measure intensity of an equal portion of the emitted light and each can measure a particular part of the range of wavelengths of interest by use of the associated bandpass filters. In this approach, a large fraction of the available light is made available to relatively few detectors, providing enhanced sensitivity at the specific wavelengths to be measured. Moreover, the relative sensitivity of the four detectors is unimportant to the method and apparatus, making it possible to use PMTs, which are ultra sensitive to light.

Each PMT 42, 44, 46, 48 is exposed to, and measures, a different and specific wavelength of light that is close to the wavelength of the Raman signal for carotenoids based on the light emitted by the light sources 20, 22. Thus, where the LEDs 20, 22 emit light at wavelengths of 471.3 to 473.0 nanometers, the analyzer filters 54 may center on 505.8, 507.8, 509.8, and 511.8 nanometers. In a particular embodiment, each filter 54 has a one nanometer pass band width. However, different pass band widths and different center wavelengths could be used. Accordingly, the first PMT 42 may measure light at 505.8 nanometers; the second PMT 44 may measure light at 507.8 nanometers; the third PMT 46 may measure light at 509.8 nanometers; and the fourth PMT 48 may measure light at 511.8 nanometers.

The output from each PMT is communicated to an analysis component of the apparatus to determine the level of carotenoids present in the tissue. In a specific embodiment, the output of each PMT is sampled 3,000 times per second and run through an analog-to-digital converter. The PMT output is communicated to the analysis component as a voltage with values ranging from 0 to 10 volts. This voltage correlates to the amount of light to which the PMT is exposed.

A measurement takes place as follows: The light source that is filtered to 471.3 nanometers is turned on and it illuminates the tissue sample, causing a Raman signal to be generated at 507.8 nanometers as well as a strong amount of unwanted fluorescence background light. The four PMTs measure a wavelength proximate to the expected Raman shift wavelength generated and emitted from the sample. For example, the four PMTS may measure 505.8 nanometer light, 507.8 nanometer light, 509.8 nanometer light, and 511.8 nanometer light respectively. The vast majority of this light is fluorescence. However, the PMT observing 507.8 nanometer light sees a small amount of additional light due to the Raman signal. An average reading on each PMT is obtained during a measurement interval and recorded. The light source filtered to 471.3 nanometers is then turned off, and the light source filtered to 473.0 nanometers is turned on. The measurement is repeated. The fluorescence levels observed at each PMT are similar, but the small amount of Raman signal now appears as additional light at the PMT measuring 509.8 nanometers. This measurement sequence can be iterated and averaged to reduce noise in the average readings of the PMTs (eight readings total, each PMT being read during illumination of the sample with each light source). Next, the four PMT readings obtained with 471.3 nanometer illumination of the sample are divided, respectively, by the four PMT readings obtained with 473.0 nanometer illumination of the sample. This generates four numbers whose values are close to 1, because the two groups of four PMT readings are dominated by fluorescence and are very similar. However, the number generated for the PMT observing 507.8 nanometer light will be slightly greater than 1, for example 1.005, due to the extra Raman signal in the first measurement, and the number generated for the PMT observing 509.8 nanometer light will be slightly less than 1, for example 0.995, due to the extra Raman signal in the second measurement. This difference from 1 reveals the ratio of the Raman peak to the fluorescence in the sample. A subsequent multiplication by the average level of fluorescence yields a number proportional to the amount of carotenoid molecules in the sample.

While the above measurement description is specific to a first light source filtered to 471.3 nanometers and a second light source filtered to 473.0 nanometers, it is to be appreciated that the light sources may be filtered to any suitable wavelength.

The calibration portion 16 comprises a light source 23 for emitting a light used only for calibration of PMT response to remove effects of drifts that occur with temperature changes or changes in applied voltage. The wavelength of the light emitted by the light source 23 corresponds generally to the wavelength of the light expected to be received from the tissue for processing by the analyzer portion 14. Thus, the light emitted by the light source 23 may be LED light ranging from approximately 505 nanometers to approximately 512 nanometers. The light passes through a filter 56. The filter 56 may comprise, for example, a neutral density filter. The neutral density filter 56 reduces the power of the light to a level comparable to light returning from the tissue in the Raman measurements. A photodiode 58 is provided in the calibration portion 16. The photodiode measures light within the cavity through which the calibration light passes.

The light from source 23 is directed through a light beam delivery system to the central optical axis and toward the analyzer portion 14. The light beam delivery system may comprise any combination of optical components for directing light to PMTs to be measured. As shown, the light beam delivery system comprises the dichroic mirror 34, which, even though it is designed to transmit light in the 505 to 512 nanometer range, reflects a small amount of the light. Thus, the light from the light source 23 passes through the filter 56 and is directed by the dichroic mirror 34 onto the central optical path 60 and to the analyzer portion 14.

FIGS. 2-8 show an exemplary physical layout for commercial product that embodies the components shown schematically in FIG. 1. This layout includes internal housings (generally 70) for various components discussed, which may then be enclosed in an external housing 900 suitable for a portable version of the product. Such a version makes it relatively easy to place a hand or other tissue immediately against the end of the glass rod 40. A temperature sensor (not shown) may be provided at or near the PMTs 42, 44, 46, 48 for sensing PMT temperature. FIGS. 9-14 show the external housing and the various internal housings and structures. While FIGS. 9-14 show the general location of components, for simplicity they do not attempt to show the light path as it appears in FIG. 1.

Supporting Electrical Components

The above described light handling components cause the excitation light used in the apparatus to be generated and directed and cause the emitted light to be received, directed and measured to produce raw emission values. These components have associated support and control components, including software, that are necessary to carry out the methods of operation discussed below. The support and control components may be located in part within a housing 900 (see FIG. 9) for the light handling components and in part on separate computer 200 (see FIG. 2) or data processor that communicates with the support and control components contained within the housing for the light handling components of the apparatus 10. A fan 203 (see FIGS. 5 and 6) may be included for cooling the components.

The computer 200 may control such functions as powering the apparatus 10 on and off, adjusting the voltage to the PMTs, adjusting the current to the light sources, switching individual light sources on or off, and reading the values output by the PMTs, the photodiodes, and a temperature sensor. The computer 200 may also receive raw data that is digitized and prepared for the various steps of the data analysis. Alternatively, data processing components (microprocessors, DSPs or other logic components) can be located on circuit boards 1210, 1212 and 1214 (see FIG. 12) within the housing 900. These data processing components can do all or most of the processing and pass to the computer 200 a small set of results data that requires little or no further computation but may be displayed for a user's review, storage or further communication.

The functions of the support and control components include: supplying power to the excitation light sources 20, 22 and the calibration light source 16 and sensing, controlling and adjusting the current supplied; supplying power to the photomultipliers and sensing, controlling and adjusting the voltage supplied; reading the output voltages or other values that are the outputs of PMTs 42, 44, 46, 48, photodiodes 38 and 58 and temperature sensor (not shown); digitizing voltages and other values sensed and formatting them for communication to digital processing components, actuation of any possible mechanical components, storing and communicating data; and receiving and executing control signals from the user interface and from software that control the operating sequences of the apparatus and any available component and system testing. These can be performed by conventional components configured to operate with the control software that implements the methods discussed below and with the light handling components discussed above.

Power for all support and control components within the housing 900 is supplied at connector 1412, for example from power source 201 (see FIG. 2), while communications to and from computer 200 are made over a communication channel connected to the housing 900 at connector 1410. Power can also be provided by an internal source, such as a battery, and the communication channel may be a physical or wireless connection.

Discussion of Methods

Figure 15:
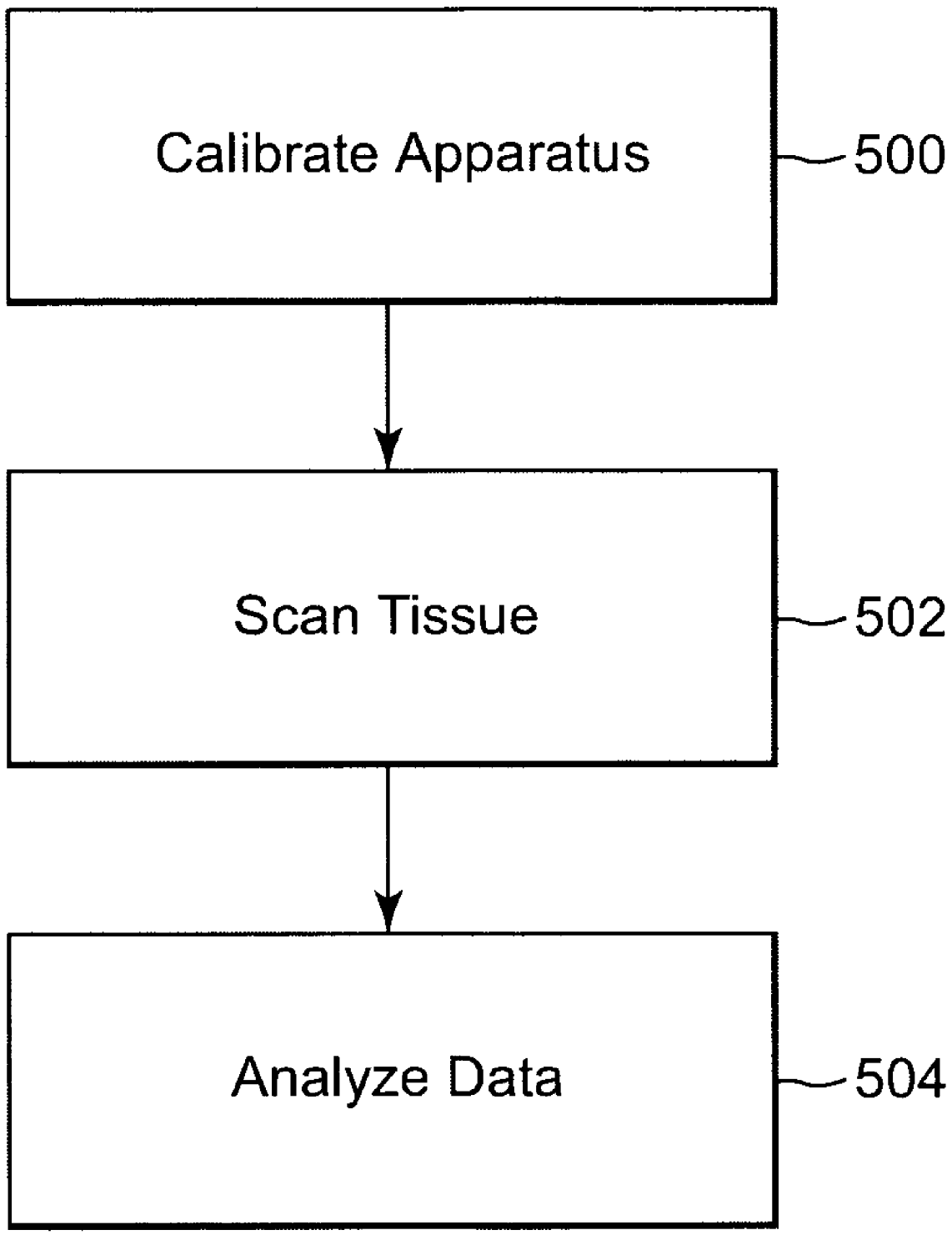
FIG. 15 is a high-level flow chart of the methods used with the apparatus.

As shown in the high-level flowchart of FIG. 15, the three overall methods used in operation of the apparatus are: calibration of the apparatus, shown at block 500; measuring light scattered from tissue or another target from two excitation wavelengths, shown at block 502; and analysis of the data from these two measurements to get a final value for the carotenoid level, shown at block 504. Each of these methods is discussed below.

1. Calibration

These materials may be prepared, for example, by the methods of and using the compositions discussed in U.S. patent application Ser. No. 10/98 1139, filed Nov. 3, 2004, issued as U.S. Pat. No. 7,365,839 on Apr. 2, 2008, titled Process and Compositions for Synthetic Calibration of Bio-Photonic Scanners, herein incorporated by reference, or by other methods as known in the art.

Calibration may be done as often as desired but is generally done prior to tissue measurements and is done less frequently than tissue measurements. The data and operating parameters from the calibration are used to analyze the data as described later in this document.

Figure 17:
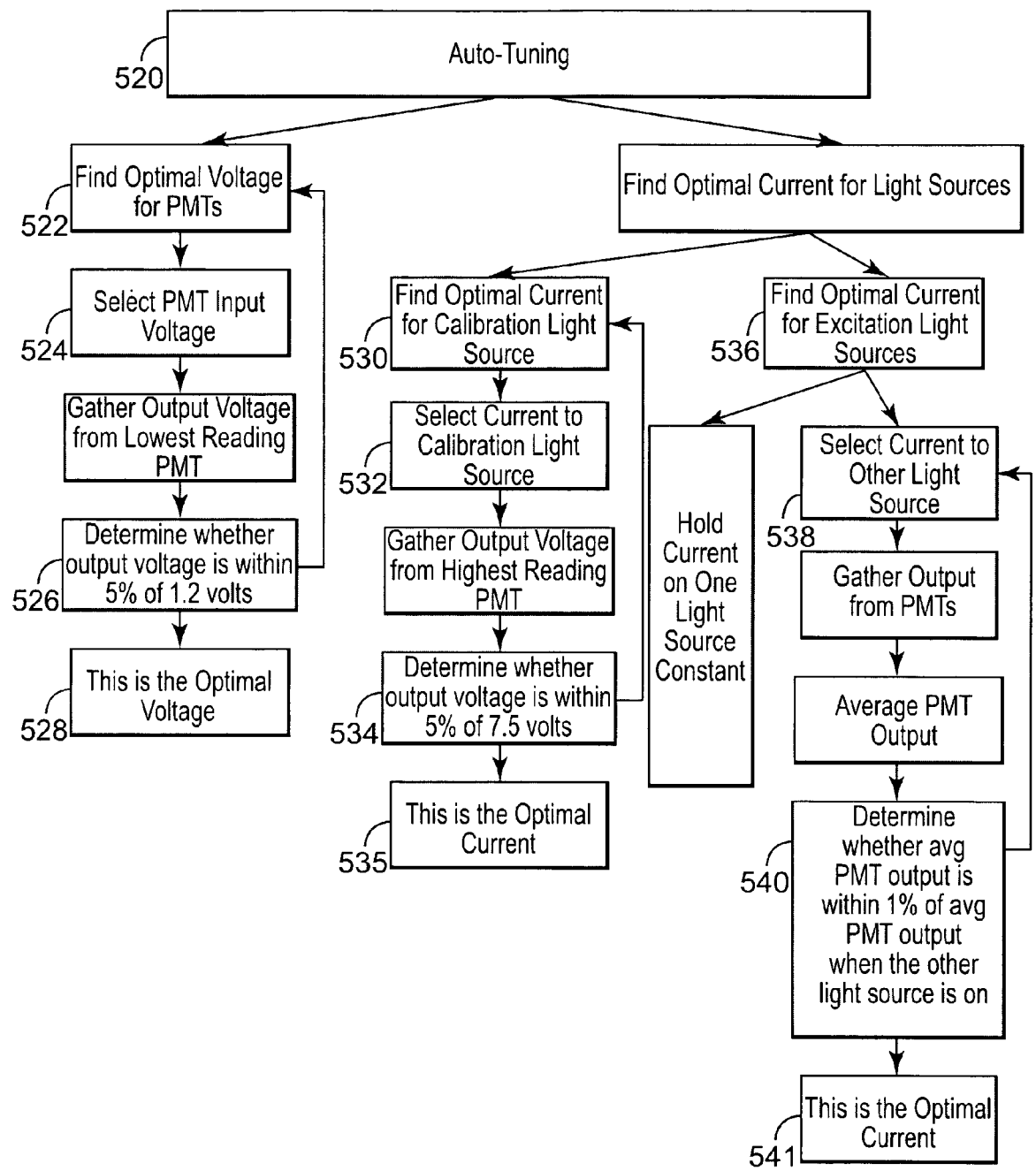
FIG. 17 is a flow chart of the auto-tuning portions of the field calibration process used with the apparatus.

A portion of the calibration process known as "auto-tuning" 520 is diagrammatically shown in FIG. 17. Auto-tuning is used to determine optimal settings for the PMT input voltage and the light source current. In general, the first and second light sources 20, 22 produce different light output levels when operated under identical conditions. In a specific embodiment, the current for the first and second light sources 20, 22 and the input voltage for each PMT are initialized to typical settings.

To determine optimal voltage, starting at box 522, a reference standard material is illuminated using one of the light sources 20, 22. The PMT input voltage is changed, shown at box 524, until the output value of the lowest PMT is within 5% of 1.2 volts, determined at box 526. At this input voltage, the PMTs will get good quality readings of the reference standards and most tissue (as discussed below, fine tuning of PMT voltage may be needed to perform measurements on tissue having unusually high fluorescence). Thus, as shown at box 528, this is an optimal voltage.

To determine the optimal current level for the calibration light source, starting at box 520, the current level for the calibration light source 23 of the calibration portion 16 is adjusted, shown at block 532, until the output voltage of the highest reading PMT is within 5% of 7.5 volts, determined at box 534. As shown at box 535, this is an optimal current.

To determine the optimal current level for the first and second excitation light sources 20, 22, starting at box 536, the light source current used for the first and second light sources 20, 22 is adjusted, shown at box 538, until the average PMT output voltage measured while illuminating the reference standard material when one light source is on is within 1% of the average when the other light source is on, determined at box 540. As shown at box 541, this is an optimal current.

Generally, the values derived in the auto-tuning process vary only slightly from day to day. The process eliminates the need for calibration at the factory and adapts as the apparatus ages or is operated in different environments.

Reading an optically dark material (a "dark scan") provides a baseline measure of the optical and electrical signal in the absence of external sources of fluorescence. This may be referred to as "dark data." A black-anodized lens cap 1211 (see FIG. 12) may be provided with the apparatus for use as an optically dark material. The output values of the PMTs with the dark material as target are saved for use later in data analysis (described below). The dark data is captured for each of the first and second light sources 20, 22 by switching the light sources on and off. The "dark data" values are subtracted from the raw data from all subsequent readings of the PMTs. These values are typically small when compared to the values captured when other calibration materials or tissues are read.

Measuring a reference standard material can be used to compute an un-calibrated score that may be referred to as "C". A reference material having a Raman response at 509 nanometers that is on par with very high reading tissue is measured using the apparatus. The data from the measurement of this "high" reference material is analyzed to compute the un-calibrated score. The C-value for the high reference material is carried forward into computing the coefficients of a linear equation for use in data analysis. The calibration process may also use a higher-order equation for the data analysis.

In a particular embodiment, a calibration process computes a coefficient and offset for a linear equation used to compute the Carotenoid Score from the C-values of measurements of tissue. The equation is discussed more fully below in relation to Data Analysis. A high calibration standard target sample, referred to previously as the high reference material, is assigned a nominal Carotenoid Score of 77,000. This number is arbitrary and may be varied. However, the number allows a broad tissue sampling to score between 0 and 100,000 using a scale that reflects the relative carotenoid content in the tissue. In a particular embodiment, C-values are mapped to this scale by a simple linear equation which is the slope-intercept formula for a line.

$$\text{Carotenoid Score} = C\text{-value} * \text{coefficient} + \text{offset}$$

The coefficient is computed by dividing the assigned (nominal) value of the high reference standard by the C-value obtained when it is read. Normally, a second reference standard may be read to give two points to use in computing the coefficient and offset of the line. The apparatus, however, gets a C-value sufficiently close to zero when reading a reference sample that contains no Raman active material that the second point can be assumed to have an assigned value of zero and a C-value of zero. Thus, the formula for computing the coefficient needs only one reading and the offset is zero. The calibration is a single-point calibration, rather than a more complicated and time-consuming two-point calibration. Additional measurements can be made using standard reference materials with different assigned scores to generate higher-order calibration equations.

Several other values may be captured during calibration for use in normalizing raw data during data analysis. These include but are not limited to: (a) a reading of the cyan/green photodiode 58 of the calibration portion 16 (the "green diode calibration reading"); (b) a reading the output voltage of each of the PMTs while the calibration light source 23 is auto-tuned (referred to as "green calibration data"; and (c) a reading of the photodiode 38 of the excitation portion 12 is captured for the first and second light sources 20, 22 during the reading of the high reference material (the "first blue diode calibration reading" and the "second blue diode calibration reading" for the first and second light sources, respectively).

A check may be performed at the end of the calibration process to determine if the apparatus is "zeroing." This measures the machine's ability to produce quality readings. A machine that properly zeros gets a C-value near zero when reading a reference material that has fluorescence but no Raman signal at the same wavelength as carotenoids (for example, 509 nanometers). The data to make this check is captured during the auto-tuning process. Because the C-value is not computed until after the dark data has been captured, the "zeroing" check is performed at the end of the calibration process.

2. Scan and Measurement

Figure 18:
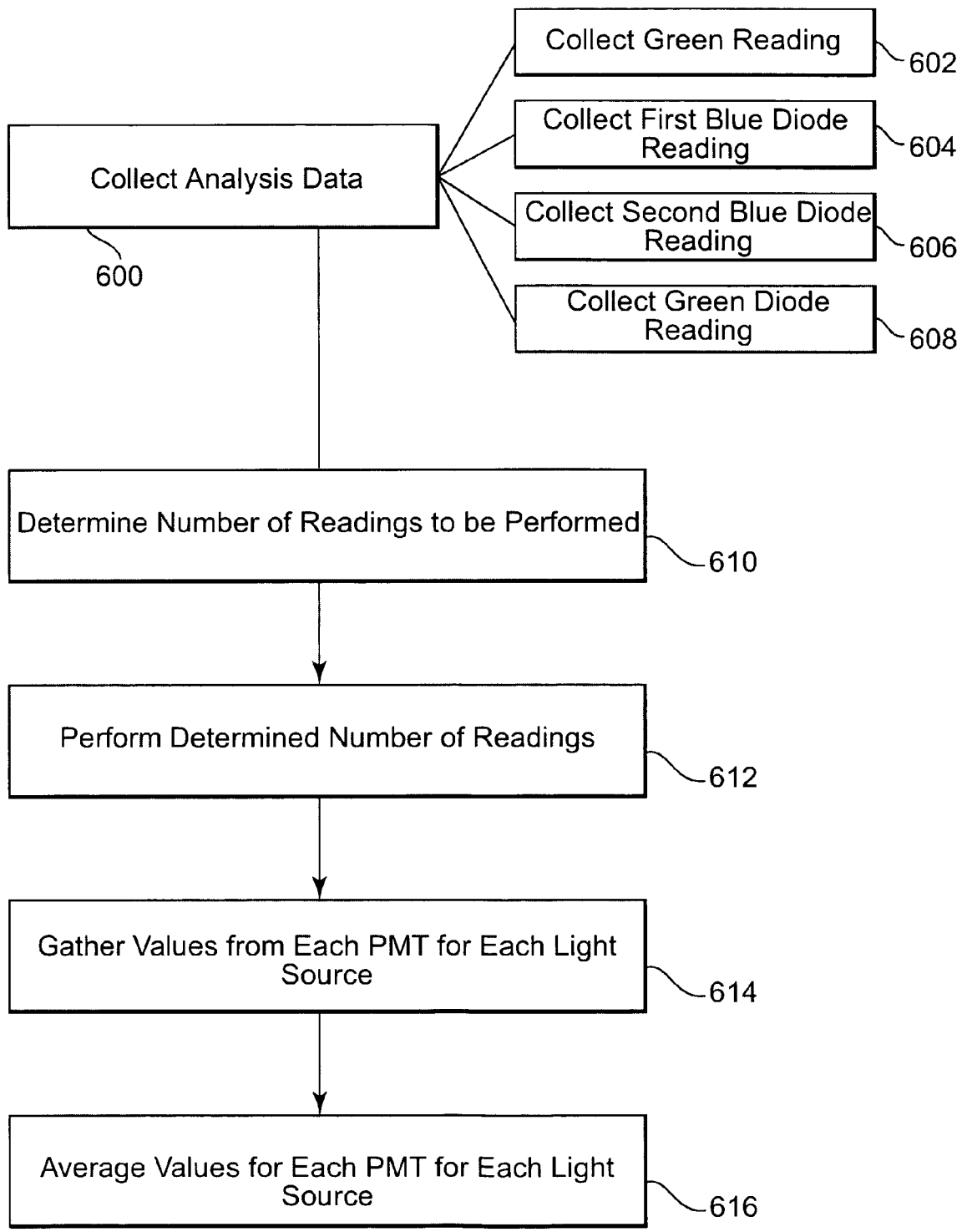
FIG. 18 is a flow chart of the data gathering and initial computations used to collect readings in tissue measurements.
Figure 19:
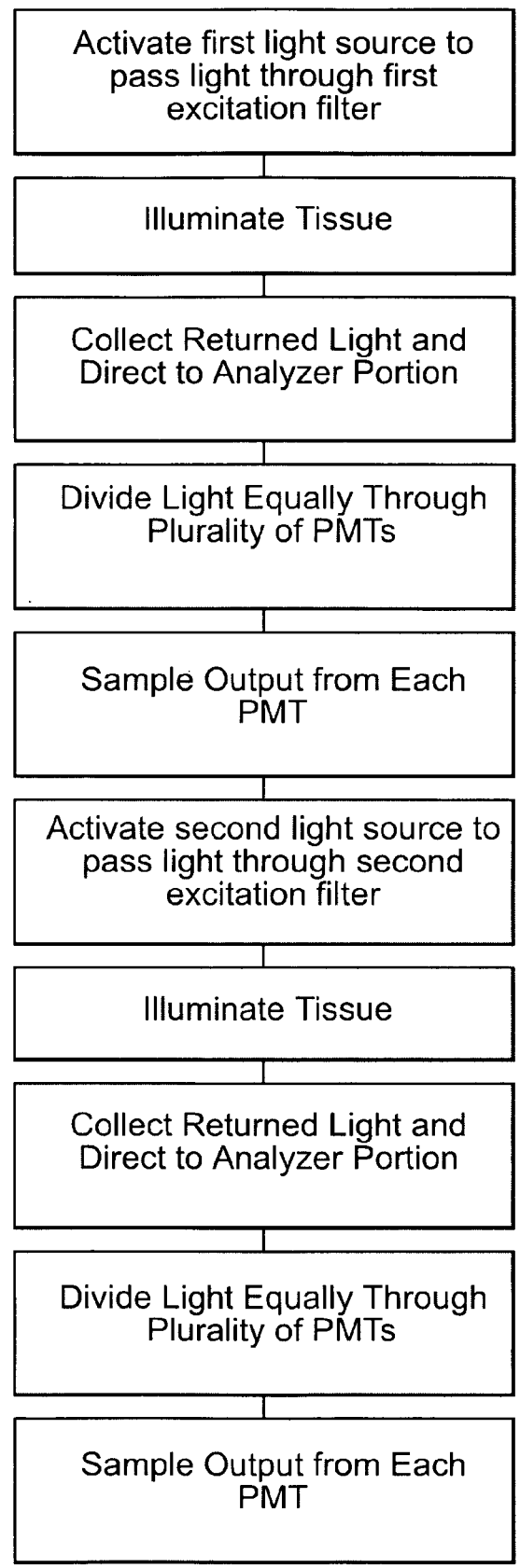
FIG. 19 is a flow chart of the steps for performing the two scans needed to provide measurements that are analyzed to produce a final Raman scattering value.

FIG. 18 broadly illustrates the process of scanning and measurement. Before conducting each scan of tissue, data is collected, shown at block 600, for use during Data Analysis (described below). A "green reading" is gathered, shown at block 602, by illuminating the green/cyan light source 23 of the calibration portion 16, directing the light through the analysis portion 14, and processing the light with the PMTs. The output of each of the PMTs is gathered and comprises the "green reading" for the scan. A "first blue diode reading" for the first light source 20 of the excitation portion 12 (block 604), a "second blue diode reading" for the second light source 22 of the excitation portion 12 (block 606), and a "green diode reading" for the light source 23 of the calibration portion 16 (block 608) are gathered by separately illuminating the respective light source and taking the value at the associated photodiode 38 or 58.

During operation of apparatus 10, the first light source 20 is activated to generate a first excitation light. The light is directed through an excitation filter (for example, the narrow-band filter 24) and through the light delivery system to the tissue or other target. The current to the first light source 20 may be adjusted to control its brightness. A short delay may be provided to allow the output from the first light source 20 to stabilize. The backscattered light from the tissue is passed through the light collection system to the analyzer portion 14. The light is divided equally and directed to the PMTs. The output of each PMT is sampled, for example at a rate of 3,000 samples per second over an interval of 100 milliseconds. The PMT output at each sample is converted from analog to digital and reported as a voltage. A value is collected for each of the PMTs. This process is then repeated with the second light source 22.

The current applied to each of the first and second light sources 20, 22 may be different. Generally, it is desirable that the intensity of the light as directed to the tissue be the same from each of the light sources 20, 22. To do this, the light sources may be driven at different currents, because there is a difference between the brightness of the two light sources and a difference in the transmission efficiency of the two excitation filters. The optimal current for each light source may have been determined in the "auto-tuning" portion of the calibration process. As previously discussed, such optimal current is not necessarily determined for each individual scan.

The voltage applied to the PMTs may also be determined during the auto-tuning process. Generally, the PMT voltage is set to a value that produces an output from the PMT that is high enough to give a good reading of the reference standard materials (described above) without being so high that the analog-to-digital converter saturates when reading tissue having high fluorescence.

A reading is developed using two measurements—one from the first light source 20 and one from the second light source 22. Thus, in one embodiment, to develop a reading, a first measurement is taken with the first light source through a 471.3 nanometer excitation filter. Thus, the first measurement corresponds to illumination of the target with light of a first wavelength F1. Four PMT values, one from each PMT, from this first measurement are saved. A second measurement is taken with the second light source through a 473.0 nanometer excitation filter. Thus, the second measurement corresponds to illumination of the target with light of a second wavelength F2. Four PMT values, one from each PMT, from this second measurement are saved. Thus, the reading uses eight values: four PMT values measured with a 471.3 filter and four PMT values with a 473.0 filter. (As will be obvious to one skilled in the art, a different number of PMTs may be used with a different number of values being used for the reading. A characteristic Raman emission wavelength Fc is associated with the selected molecule to be measured in the tissue. Each PMT samples the light intensity at a wavelength at or adjacent to the expected emitted light wavelength and thus provides data on the target fluorescence in the vicinity of the wavelength at which it is desired to measure only the Raman scattering signal.)

The plurality of PMTs are read concurrently by a controller computer or data processing components, e.g., programmed microprocessor, DSP or other logic components. The values from the PMTs are captured for a measurement using the first light source 20. The values from the PMTs are then captured for a measurement using the second light source 22. The two sets of measurements, i.e., sampled intensity values of sampled, emitted light resulting from illumination using the first and second light sources 20, 22, together represent a single reading. Multiple readings are performed for each light source 20, 22 and the results are averaged to gather the eight values of raw data for a complete scan. The values are collected and averaged to smooth out small variations that may occur from one measurement to the next.

Thus, a first set of sampled intensity values is developed for light resulting from the illumination of the target with light of the first wavelength F1 and a second set of sampled intensity values is developed for light resulting from the illumination of the target with light of the second wavelength F2. The controller data processing logic and PMTs programmed to develop the two sets of sample values thus comprise a first sampler for emitted light resulting from the first light source and a second sampler for emitted light resulting from the second light source. Each set includes a value at or near the characteristic emission wavelength Fc associated with the selected molecule and the respective wavelength F1 or F2. Each set further includes at least two values adjacent the characteristic wavelength Fc but sufficiently displaced from that wavelength to exclude Raman emissions resulting from the respective wavelength F1 or F2. At least one of these values is below the expected characteristic wavelength Fc and at least one of the values is above the expected characteristic wavelength Fc. Each set of intensity values comprises a value from each intensity sensor (for example, PMT). Thus, the first set of sampled intensity values includes values from a plurality of sensors resulting from the illuminations for the first wavelength F1. For example, the first set may comprise four values, SF10, SF11, SF12, SF13, one resulting from each of four sensors. The set of values is an ordered set and one of the values, for example SF11, is a measurement at characteristic wavelength Fc associated with the selected molecule and the first wavelength F1. Similarly, the second set of sampled intensity values includes values from a plurality of sensors resulting from the illuminations for the second wavelength F2. For example, the second set may comprise four values, SF20, SF21, SF22, SF23, one resulting from each of four sensors. The set of values is an ordered set and one of the values, for example SF21, is a measurement at characteristic wavelength Fc associated with the selected molecule and the second wavelength F2.

Thus, a complete scan and measurement comprises: (1) determining the number of readings to be performed, shown at block 610, (generally, it takes more readings and longer scans to get good results when reading skin than when reading reference standards; the number of scans to be performed may be readily determined by ordinary experimentation by one skilled in the art); (2) adjusting the voltage to the PMTs to the value determined during the auto-tuning process; (3) performing the determined number of readings and saving the eight values returned from each, shown at blocks 612, 614; and (4) averaging the results of the eight values returned from each measurement, shown at block 616. The raw, unprocessed data from a scan thus comprises averaged values of each PMT with each light source for a total of eight values. (Note that the step of adjusting the PMT voltages need not be performed unless these have been changed since the calibration process has been rerun.)

As will be discussed below, the raw, unprocessed data undergoes data analysis for conversion into a Carotenoid Score. Generally, an interpolated intensity value for emitted light between the characteristic wavelength Fc associated with each of the first and second wavelengths F1 and F2 is derived from the first and second sets of sampled intensity values. The interpolated intensity value removes the intensity value component due to the non-Raman emissions.

It should be noted that tissues exhibiting unusually high fluorescence may generate such a high output from the PMTs that the analog to digital converter cannot correctly convert the value. When this happens, the PMT voltage may be reduced by approximately 20 volts and the scan repeated. The voltage may be repeatedly reduced in steps of approximately 20 volts until the scan succeeds. The green diode signal can be read again and compared with previous green diode readings to properly calibrate tissue readings at reduced PMT voltages.

3. Data Analysis

A data analysis process converts the raw data obtained in the readings to a Carotenoid Score. The Carotenoid Score may be expressed on any range and indicates the level of carotenoids in the tissue. In one embodiment, the range is from 0 to 100,000. As previously set forth, a calculation of the Carotenoid Score is:

Carotenoid Score=C-value*coefficient+offset

The analysis process uses data gathered during calibration to process the raw data from the current scan.

As discussed above, the current scan results in a plurality of values: a value for each PMT using the first light source and a value for each PMT using the second light source. In the embodiment discussed, thus, the scan results in eight values: a value for each of four PMTs using a light source with a 471.3 nanometer filter and a value for each of four PMTs using a light source with a 473.0 nanometer filter. The values each comprise an averaging of the readings of each PMT, representing samples at different wavelengths in the wavelength range covered by the PMTs and their bandpass filters.

Temperature variations may occur due to changes in the environment in which the scans are being done, or due to the simple warming of the machine and the PMTs during normal operation. "Green Normalization" is performed on the raw data to correct for any change in the light-sensitivity of the PMTs and resultant change in the response of the PMTs. Green normalization comprises adjusting (multiplying) the raw data by the ratio of the green calibration data (PMT readings of the light source of the calibration portion taken at calibration, as shown at 516 of FIG. 16) divided by the green reading (the PMT readings taken at the beginning of the scan with the light source of the calibration portion illuminated, as shown at 602 of FIG. 18). This procedure adjusts the raw PMT readings to what they would have been had the scan taken place at the time of calibration.

While green normalization corrects for changes in PMT response, brightness calibration is done to correct for changes in the brightness of either light source 20 or 22. In one embodiment, PMT readings taken with the first or second light sources 20, 22 of the excitation portion 12 may be corrected by multiplying the PMT signal by the ratio of the corresponding blue LED signal measured during the calibration process to the blue LED signal measured during the tissue reading.

Thus, the raw data is corrected for changes in PMT response (for example due to temperature change) and light source brightness that may have occurred between the time the machine was calibrated and the time the scan was run. PMT voltages are corrected using the change in the reading of the light source 23 of the calibration portion 16. Light source brightness is corrected using changes in the readings of the blue photodiode 38.

The photodiode readings may also be corrected. When the light sources 20, 22, 23 are switched off, there should be no light in the system and the photodiodes should read zero. This is not always the case. Thus, at the beginning of a scan, the light sources 20, 22, 23 may be switched off and a brief reading is taken of the non-zero voltage at the photodiodes 38, 58. The non-zero voltage measured may then be subtracted from all subsequent photodiode readings made within the same scan.

All PMT readings are "dark subtracted" during data analysis. The dark data from the dark scan is used during dark subtraction. Each of the raw data values that were saved from the dark scan is subtracted from its counterpart in the normalized data array (i.e., the Dark value at PMT 42 with first light source 20 and filter 24 is subtracted from normalized data at PMT 42 with first light source 20 and filter 24). In one embodiment, the dark data is not normalized or corrected at the time of capture or at the time it is applied.

For each PMT, the ratio of the dark-subtracted, green-normalized raw data captured when the first light source (for example, having a 471.3 nanometer excitation filter) was illuminated is divided by the equivalent data when the second source (for example, having a 473 nanometer filter) was illuminated. In the embodiment shown, this process generates four normalized signal ratios, one for each PMT. These ratios, thus, may comprise SF10/SF20, SF11/SF21, SF12/SF22, and SF13/SF23. A value "D" is computed using these four ratios.

Figure 20:
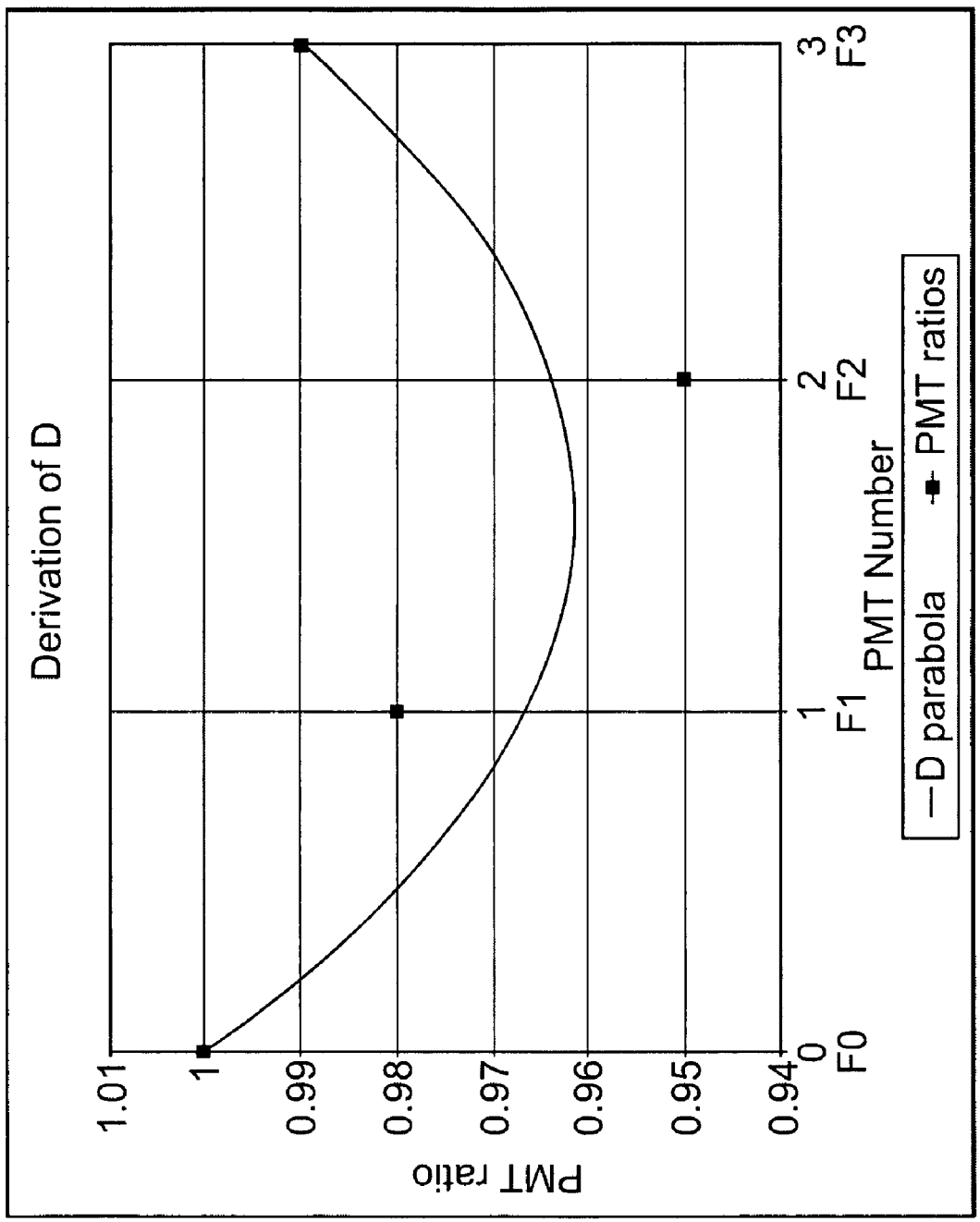
FIG. 20 is a chart showing graphing of PMT ratios for measurements at two different excitation wavelengths and a parabolic curve constructed using the ratio values.

D is a measure of the difference between the ratios of the PMTs in the presence or absence of a carotenoid signal. It is the difference in the signal that carotenoids add over and above the target fluorescence measured by the machine. "D" is computed relative to a parabola drawn through the four ratios, shown in FIG. 20. The parabola has two properties. First, the parabola passes through the ratios of the first and last PMTs. Second, the magnitude of the distance between the ratio and the parabola for the second PMT is equal to the magnitude of the distance at the third PMT. FIG. 20 shows the PMT ratios and the parabola that is derived from them. D is the distance from the PMT ratio down to the curve for PMT1 or up to the curve for PMT2. In the algorithm embodiment shown these distances are equal. The equation for the parabola used in this interpolation algorithm is discussed more fully below.

Generally, a parabolic curve is used to interpolate between two known endpoints (PMT0 and PMT3) to find the target fluorescence level midway between PMT1 and PMT2. This level may be used to determine the value of D. The ratios measured at PMT0 and PMT3 are thus used in a parabolic interpolation algorithm to determine the target fluorescence at the midpoint of the spectrum (wavelength sampling range) measured between PMT0 and PMT3. This procedure returns a value D that is the magnitude of the difference between the ratio measured at PMT1 and the background fluorescence signal level and/or the magnitude of the difference between the ratio measured at PMT2 and the background fluorescence signal level.

Stated otherwise, a curve is extrapolated to fit the computed ratios, the curve passing through the points {f0, SF10/SF20} and {f0, SF13/SF23} where each of f0, f1, f2, and f3 is a center wavelength for a respective first, second, third, and fourth of the four sensors and the curve is equidistant from the points {f1, SF11/SF21} and {f2, SF12/SF22}.

Thus, the value D represents a measure of the difference between the ratios of the readings of the PMTs when the Raman signal is present and when it is not. This difference is the difference in the signal that carotenoids add over and above the target fluorescence measured by the apparatus. This value indicates the relative carotenoid concentration level in the target. D is a very small number, reflecting the fact that the Raman signal is very small compared to the background fluorescence. Normally, D will be close to zero when reading a reference standard with no Raman active ingredients. D can be over 0.02 when reading a reference standard that contains material that produces a significant Raman signal. D for skin tissue is typically in the range of 0.0050 to 0.0100. The specific value is influenced by the spectral resolution of the sensors or detectors, which in this embodiment are a set of PMTs.

Generally, as discussed more fully below, to compute D, a parabola is drawn through the PMT ratios. The parabola has two properties. First, the parabola passes through the ratios of the first and last PMTs. Second, the distance between the ratio and the parabola for the second PMT is equal to the distance between the ratio and the parabola at the third PMT. D is the distance from the PMT ratio down to the curve for the second PMT or up to the curve for the third PMT (these distances are equal).

Thus, D measures the increase in the PMT ratio due to the presence of the Raman signal. Because D was calculated using ratios of PMT signals, creating a meaningful measure of the amount of Raman active material present requires multiplying D by the average PMT voltage measured when the second light source illuminated the second filter. This value is called C and is the final, un-calibrated measure of the amount of Raman active material in the tissue.

In the final step, the Carotenoid Score is computed from the value of C obtained from the scan and the Coefficient and Offset generated by the Calibration process. This produces a calibrated Carotenoid Score. The calibration process mitigates the changes that may occur from day-to-day within a machine or from one machine to another. Components age and are never identical from one machine to the next. The calibration process prevents these things from affecting scores.

A generally linear relationship is found when reading the reference standards between increasing concentrations of active material and C-values. The linear equation is thus used to compute the final result of a scan:

Carotenoid Score=(C*Coefficient)+Offset

In another embodiment, higher order polynomials may be used in representing the calibration material readings with increasing concentrations of active materials.

It is to be noted that with four PMT measurements, the curve fit can only be linear or parabolic. However, if the number of PMTs were increased, a polynomial up to the number of PMTs—2 may be created. Thus, for example, if five PMTs are provided, a third order polynomial may be fit.

Further, while two excitation wavelengths are used, any number of excitation wavelengths may be used.

Benefits and Uses

The method and apparatus may be used to detect and measure carotenoid content in tissue such as human skin. Using data from more than two million scans with similar equipment and calibration, the average Carotenoid Score of human skin is 26,000. There is a high correlation between diets high in fruits and vegetables and Carotenoid Score. People with healthy diets and who use nutritional supplementation may score above 70,000. People with poor eating habits or other behaviors such as smoking sometimes score below 10,000.

It has been previously demonstrated in some research that there is a correlation between the levels of carotenoids, retinoids, and similar chemical substances in the skin and certain health conditions. If low levels of carotenoids are measured, preventative steps can be taken, such as dietary corrections, including dietary supplements.

Several of the carotenoids that have been found to be associated with good health include all-trans-.beta.-carotene, lycopene, .alpha.-carotene, .gamma.-carotene, phytoene, phytofluene, septapreno-.beta.-carotene, 7,7' dihydro-.beta.-carotene, astaxanthin, canthaxanthin, zeaxanthin, lutein, .beta.-apo-8'-carotenal, violaxanthin, and rhodoxanthin. These are chain-like molecules with different lengths and attachments, all having a carbon backbone with alternating carbon double and single bonds, respectively. The vibration of these bonds, common to all carotenoids, can be detected with Raman spectroscopy. It is known from separate measurements that the wavenumber shifts of these carotenoids are generally in the range from 800 to 2000 $cm^{-1}$ (wavenumbers). For example, the carotenoids lutein and zeaxanthin are known to have wavenumber shifts of approximately 1160 $cm^{-1}$ and 1520 $cm^{-1}$, respectively.

Carotenoids are an important component of the skin's antioxidant defense systems, where they are thought to act as free radical and singlet oxygen scavengers. Furthermore, carotenoids protect the skin from a number of harmful reactive oxygen species (ROS), which are formed, for example, by excessive exposure of skin to ultra-violet (UV) light such as from sunlight. Once formed, the ROS efficiently react with DNA, proteins, and unsaturated fatty acids, causing DNA strand breaks and oxidative damage, as well as protein-protein and protein-DNA cross links. Oxidation of lipids can result in the formation of lipid peroxides which persist a relatively long time in the cells and can thus initiate radical chain reactions and enhance oxidation damage.

The method and apparatus provides for a rapid, non-invasive assessment of carotenoid levels in a variety of human tissues and bodily fluids and has further beneficial uses. These include assessing the overall antioxidant status in human tissue; providing for monitoring of dietary manipulation of tissue carotenoid or other antioxidant content; and providing a tool to assess carotenoid distribution and uptake from cosmetic compounds.

Further, the method and apparatus may be used in measuring the carotenoid levels in skin and skin lesions. The intensity of the light scattered inelastically from the carotenoid molecules and forming the Raman signal can be compared with the intensity of Raman scattering from normal biological tissue to assess conditions. The intensity of the Raman signal can also be quantified to assess the antioxidant status of the tissue.

Deriving "D"

The following discussion starts with the general form of the equation for a parabola and (x, y) pairs of points whose values are the PMT number and the ratio of its output values when the 471.3 filter is used for the reading divided by the value when the 473.0 filter is used. The discussion shows derivation of equations that may be used to compute D and the coefficients of the baseline parabola. Reference should be made to FIG. 20.

P0, P1, P2, and P3 are the values of the ratios at PMTs 0 to 3, respectively. Four points on the parabola are known.

$(x_0, y_0) = (0, P_0)$ $(x_1, y_1) = (1, P_1 - D)$ $(x_2, y_2) = (2, P_2 + D)$ $(x_3, y_3) = (3, P_3)$

Using these values, and the general form for the equation of a parabola ($y = ax^2 + bx + c$), it is possible to solve for D.

when $x_0 = 0$ and $y_0 = P_0$, $P_0 = a(0^2) + b(0) + c$ when $x_1 = 1$ and $y_1 = P_1 - D$, $P_1 - D = a(1^2) + b(1) + c$ when $x_2 = 2$ and $y_2 = P_2 + D$, $P_2 + D = a(2^2) + b(2) + c$ when $x_3 = 3$ and $y_3 = P_3$, $P_3 = a(3^2) + b(3) + c$ In the first equation, $P_0 = c$. The above equations may be simplified by substituting c for $P_0$, moving $P_0$ to the left side, and multiplying out the constants. The four equations become:

$P_0 = c$      Equation 1

$P_1 - D - P_0 = a + b$      Equation 2

$P_2 + D - P_0 = 4a + 2b$      Equation 3

$P_3 - P_0 = 9a + 3b$      Equation 4

Thus, the value of c is resolved. D is eliminated while solving for a and b. First, solve Equations 2 and 3 for D.

$P_1 - D - P_0 = a + b$ becomes $D = P_1 - P_0 - a - b$ $P_2+D-P_0=4a+2b$ becomes $D=P_0-P_2+4a+2b$ Since D=D, the two equations may be set as equal and rearranged.

$$P_1-P_0-a-b=P_0-P_2+4a+2b$$

$$-2P_0+P_1+P_2=5a+3b \qquad \text{Equation 5}$$

Equation 5 is solved for a.

$$a=(-2P_0+P_1+P_2-3b)/5 \qquad \text{Equation 6}$$

Equations 2 and 3 are solved for a. Substitute a into Equation 4 to find b.

$$P_3-P_0=9a+3b$$

$$3b=P_3-P_0-9a$$

$$3b=P_3-P_0-9((-2P_0+P_1+P_2-3b)/5)$$

$$15b=5P_3-5P_0-9(-2P_0+P_1+P_2-3b)$$

$$15b=5P_3-5P_0+18P_0-9P_1-9P_2+27b$$

$$-12b=13P_0-9P_1-9P_2+5P_3$$

$$b=(-13P_0+9P_1+9P_2-5P_3)/12 \qquad \text{Equation 7}$$

Having found b, the simplified version of Equation 2 may be used to find D.

$$d=P_1-P_0-a-b$$

Substitute the value of a from Equation 6.

$$d=P_1-P_0-((-2P_0+P_1+P_2-3b)/5)-b$$

$$5d=5P_1-5P_0-(-2P_0+P_1+P_2-3b)-5b$$

$$5d=5P_1-5P_0+2P_0-P_1-P_2+3b-5b$$

$$5d=-3P_0+4P_1-P_2-2b$$

Finally, plug in the value of b from Equation 7 to find D.

$$5D=-3P_0+4P_1-P_2-2((-13P_0+9P_1+9P_2-5P_3)/12)$$

$$30D=-18P_0+24P_1-6P_2-(-13P_0+9P_1+9P_2-5P_3)$$

$$30D=-18P_0+24P_1-6P_2+13P_0-9P_1-9P_2+5P_3$$

$$30D=-5P_0+15P_1-15P_2+5P_3$$

$$6D=-P_0+3P_1-3P_2+P_3$$

$$D=(-P_0+3P_1-3P_2+P_3)/6$$

The result, D, may be checked by repeating the process using Equation 3.

$$D=P_0-P_2+4a+2b$$

Substituting first $a=(-2P_0+P_1+P_2-3b)/5$ then $b=(-13P_0+9P_1+9P_2-5P_3)/12$ will produce the same result for D.

$$D=P_0-P_2+4a+2b$$

$$D=P_0-P_2+4*((-2P_0+P_1+P_2-3b)/5)+2b$$

$$5D=5P_0-5P_2+4*(-2P_0+P_1+P_2-3b)+10b$$

$$5D=5P_0-5P_2-8P_0+4P_1+4P_2-12b+10b$$

$$5D=-3P_0+4P_1-P_2-2b$$

$$5D=-3P_0+4P_1-P_2-2*((-13P_0+9P_1+9P_2-5P_3)/12)$$

$$5D=-3P_0+4P_1-P_2+(26P_0-18P_1-18P_2+10P_3)/12$$

$$60D=-36P_0+48P_1-12P_2+26P_0-18P_1-18P_2+10P_3$$

$$60D=-10P_0+30P_1-30P_2+10P_3$$

$$D=(-P_0+3P_1-3P_2+P_3)/6$$

Note that this last equation for D, derived from Equation 3, is the same as that derived from Equation 2.

Note, "a" is not needed in order to compute D and is not resolved. If a baseline parabola is to be computed, "a" may be resolved. Any of the original equations may be used. For example, Equation 4.

$$P_3-P_0=9a+3b$$

$$P_3-P_0=9a+3*((-13P_0+9P_1+9P_2-5P_3)/12)$$

$$12P_3-12P_0=108a+3*(-13P_0+9P_1+9P_2-5P_3)$$

$$12P_3-12P_0=108a-39P_0+27P_1+27P_2-15P_3$$

$$-108a=-12P_3+12P_0-39P_0+27P_1+27P_2-15P_3$$

$$108a=12P_3-12P_0+39P_0-27P_1-27P_2+15P_3$$

$$108a=27P_0-27P_1-27P_2+27P_3$$

$$a=(P_0-P_1-P_2+P_3)/4 \qquad \text{Equation 4}$$

Thus, the values of a, b, c are computed, and D is given the values of the PMT ratios using the following formulas.

$$a=(P_0-P_1-P_2+P_3)/4$$

$$b=(-13P_0+9P_1+9P_2-5P_3)/12$$

$$c=P_0$$

$$D=(-P_0+3P_1-3P_2+P_3)/6$$

A final check may be performed by validating each of the four original equations.

$$P_0=c \qquad \text{Equation 1}$$

$$P_1-D-P_0=a+b \qquad \text{Equation 2}$$

$$P_2+D-P_0=4a+2b \qquad \text{Equation 3}$$

$$P_3-P_0=9a+3b \qquad \text{Equation 4}$$

$$P_0=c \qquad \text{Equation 1}$$

This is true.

$$P_1-D-P_0=a+b$$

$$P_1-((-P_0+3P_1-3P_2+P_3)/6)-P_0=(P_0-P_1-P_2+P_3)/4+(-13P_0+9P_1+9P_2-5P_3)/12$$

$$12P_1+2P_0-6P_1+6P_2-2P_3-12P_0=3P_0-3P_1-3P_2+3P_3-13P_0+9P_1+9P_2-5P_3$$

$$-10P_0+6P_1+6P_2-2P_3=-10P_0+6P_1+6P_2-2P_3 \qquad \text{Equation 2}$$

This is true.

$$P_2+D-P_0=4a+2b$$

$$P_2+((-P_0+3P_1-3P_2+P_3)/6)-P_0=4*((P_0-P_1-P_2+P_3)/4)+2*((-13P_0+9P_1+9P_2-5P_3)/12)$$

$$12P_2-2P_0+6P_1-6P_2+2P_3-12P_0=12P_0-12P_1-12P_2+$$
$$12P_3-26P_0+18P_1+18P_2-10P_3-14P_0+6P_1+6P_2+$$
$$2P_3=-14P_0+6P_1+6P_2+2P_3 \quad \text{Equation 3}$$

This is true.

$$P_3-P_0=9a+3b$$

$$P_3-P_0=9((P_0-P_1-P_2+P_3)/4)+3((-13P_0+9P_1+9P_2-5P_3)/12)$$

$$12P_3-12P_0=3*9(P_0-P_1-P_2+P_3)+3*(-13P_0+9P_1+9P_2-5P_3)$$

$$4P_3-4P_0=9P_0-9P_1-9P_2+9P_3-13P_0+9P_1+9P_2-5P_3$$

$$4P_3-4P_0=4P_3--4P_0 \quad \text{Equation 4}$$

This is also true.

Although the invention has been described with reference to preferred embodiments, persons skilled in the art will recognize that changes may be made in form and detail without departing from the spirit and scope of the invention.

The invention claimed is:

1. A method of measuring the level of a selected molecule in a target sample, comprising:
    illuminating the target with light of a first wavelength F1;
    illuminating the target with light of a second wavelength F2 adjacent to the first wavelength F1;
    receiving from the target emitted light resulting from each of the illuminations at wavelengths F1 and F2 and sampling the intensity of the emitted light at a range of wavelengths including a characteristic Raman emission wavelength Fc associated with the selected molecule and each of the illumination wavelengths;
    developing a first set of sampled intensity values for emitted light resulting from the illumination for wavelength F1, said sample including a value at or near the characteristic emission wavelength Fc associated with the selected molecule and wavelength F1, at least one sample adjacent the characteristic wavelength Fc but sufficiently displaced below that wavelength to exclude Raman emissions resulting from the illumination for wavelength F1 and at least one sample adjacent the characteristic wavelength Fc but sufficiently displaced above that wavelength to exclude Raman emissions resulting from the illumination for wavelength F1;
    developing a second set of sampled intensity values for emitted light resulting from the illumination for wavelength F2, said sample including a value at or near the characteristic emission wavelength Fc associated with the selected molecule and wavelength F2, at least one sample adjacent the characteristic wavelength Fc but sufficiently displaced below that wavelength to exclude Raman emissions resulting from the illumination for wavelength F2 and at least one sample adjacent the characteristic wavelength Fc but sufficiently displaced above that wavelength to exclude Raman emissions resulting from the illumination for wavelength F2; and
    deriving from ratios of corresponding values in the first and second sets of sampled intensity values an interpolated intensity value for emitted light between the characteristic wavelength Fc associated with each of F1 and F2 that removes the intensity value component due to non-Raman emissions, said interpolated intensity value derived from ratios of corresponding values in the first and second sets representing a measurement of the level of the selected molecule in the target sample.

2. The method of claim 1 wherein the step of developing a first set of sampled intensity values for emitted light resulting from the illumination for wavelength F1 comprises developing at least four intensity sensors a sample value resulting from the illuminations for wavelength F1 {SF10, SF11, SF12, SF13} and the step of developing a second set of sampled intensity values for emitted light resulting from the illumination for wavelength F2 comprises developing at least four intensity sensors at least four sample values resulting from the illuminations at wavelength F2 {SF20, SF21, SF22, SF23}, where each of {SF10, SF11, SF12, SF13} and {SF20, SF21, SF22, SF23} is an ordered set of values with SF11 being a measurement at characteristic emitted wavelength Fc associated with the selected molecule and F1 and SF22 being a measurement at characteristic emitted wavelength Fc associated with the selected molecule and F2.

3. The method of claim 2 further comprising adjusting each of {SF10, SF11, SF12, SF13} and {SF20, SF21, SF22, SF23} for variations in the output of the at least four intensity sensors since a calibration of such sensors.

4. The method of claim 2 further comprising adjusting each of {SF10, SF11, SF12, SF13} and {SF20, SF21, SF22, SF23} for a dark value derived from an optically dark sample target with no Raman scattering in the light emitted from the sample.

5. The method of claim 1 wherein the step of deriving from ratios of corresponding values in the first and second sets of sampled intensity values an interpolated intensity value comprises, computing the ratios {SF10/SF20, SF11/SF21, SF12/SF22, SF13/SF23} and from the resulting computed ratios, extrapolating by curve fitting to find a curve that passes through the points {f0, SF10/SF20} and {f3, SF13/SF23} on a wavelength-ratio graph and the curve is equidistant from the points {f1, SF11/SF21} and {f2, SF12/SF22} on the graph, where each of f0, f1, f2 and f3 is a center wavelength for a respective first, second, third and fourth sensor for a sampled intensity value.

6. The method of claim 5 wherein the curve fitting uses a parabola as the curve.

7. The method of claim 5, comprising from the resulting computed sample value ratios, graphically determining in a parabolic interpolation using a curve anchored at {f0, SF10/SF20} and {f3, SF13/SF23} a value that is at the midpoint of the wavelength range for the four sensors and that lies midway between the points {f1, SF11/SF21} and {f2, SF12/SF22}.

8. The method of claim 5, comprising from the resulting computed ratios, graphically determining a value that lies midway between the points {f1, SF11/SF21} and {f2, SF12/SF22} as measured by curve fitting with a non-linear curve anchored at {f0, SF10/SF20} and {f3, SF13/SF23}.

9. The method of claim 1 wherein the step of receiving from the target emitted light resulting from each of the illuminations at wavelength F1 and F2 and sampling the intensity of the emitted light at a range of wavelengths including a characteristic Raman emitted wavelength Fc associated with the selected molecule and each of the illumination wavelengths comprises directing the emitted light in predefined portions to at least four intensity sensors.

10. The method of claim 9 wherein directing the emitted light in predefined portions to at least four intensity sensors comprises directing the emitted light in equal portions.

11. The method of claim 1 wherein the selected molecule is a carotenoid.

12. The method of claim 1 wherein the target sample is human tissue.

13. The method of claim 1 wherein the target sample is tissue on a human hand.

14. The method of claim 1 where the step of illuminating the target with light of a second wavelength F2 adjacent to the first wavelength F1 and with an intensity in a predetermined relationship to the intensity of the light of first wavelength F1 comprises illuminating the target with light of a second wavelength F2 having an intensity substantially equal to the intensity of the light of first wavelength F1.

15. The method of claim 1 wherein F1 and F2 are separated by less than three nanometers.

16. The method of claim 1 wherein F1 and F2 are separated by less than two nanometers.

17. The method of claim 1 wherein the difference between the lowest wavelength value at which an emitted intensity value is sampled and the highest wavelength value at which an emitted intensity value is sampled is a wavelength range of less than 10 nanometers.

18. The method of claim 1 wherein the difference between the lowest wavelength value at which an emitted intensity value is sampled and the highest wavelength value at which an emitted intensity value is sampled is a wavelength range range of less than 7 nanometers.

19. The method of claim 1 further comprising adjusting intensity of the light of first wavelength F1 and the light of the second wavelength F2 to provide equal intensity from each light at the target when the respective light is providing illumination.

20. The method of claim 1 wherein the first and second wavelengths F1 and F2 are substantially Raman resonance wavelengths.

21. A method for measuring a chemical concentration in tissue comprising:
   generating a first light and illuminating a portion of the tissue with the first light;
   capturing a first reflected light from the tissue;
   directing the first reflected light to a plurality of light sensors, each light sensor measuring light at a different wavelength, that wavelength being proximate to a wavelength of an expected Raman shift wavelength for the chemical in the tissue;
   obtaining a measurement from each of the light sensors, each measurement being specific to the first scattered light to that light sensor;
   generating a second light different in frequency from the first light and illuminating a portion of the tissue with the second light;
   capturing a second reflected light from the tissue;
   directing the second scattered light to the plurality of light sensors, each light source measuring light at a different wavelength that wavelength being proximate to a wavelength of an expected Raman shift wavelength for the chemical in the tissue;
   obtaining a measurement from each of the light sensor; and each measurement being specific to the second scattered light to that light source; and
   using a ratio of the measurements of the first scattered light to the corresponding measurements of the second scattered light to calculate a concentration of the chemical in the tissue.

22. The method of claim 21, wherein the first and second lights are generated by light emitting diodes.

23. The method of claim 21, wherein the first and second lights are passed through first and second filters respectively.

24. The method of claim 21, wherein the first filter passes only light at 471.3 nanometers and the second filter passes only light at 473 nanometers.

25. The method of claim 24, wherein the first and second scattered lights are each divided into four equal portions and wherein the equal portions are directed to four light sensors.

26. The method of claim 25, wherein the first light sensor measures light at 505.8 nanometers, the second light sensor measures light at 507.8 nanometers, the third light sensor measures light at 509.8 nanometers, and the fourth light sensor measures light at 511.8 nanometers.

27. The method of claim 21, wherein the first and second scattered lights are directed to four light sensors.

28. The method of claim 27, wherein each of the first and second scattered lights are equally divided with an equal portion of each light being directed to each light sensor.

29. The method of claim 21, wherein using a ratio of the measurements of the first scattered light to the corresponding measurements of the second scattered light to calculate a concentration of the chemical in the tissue comprises:
   dividing the measurements from each of the light sensors specific to the first scattered light to that light sensor by the measurement from the corresponding respective light sensor specific to the second scattered light to that light sensor to obtain a Raman ratio; and
   multiplying the Raman ratio by an average level of fluorescence from the tissue.

30. The method of claim 29, wherein the average level of fluorescence is approximated by an average PMT voltage measured when the portion of tissue is illuminated with the second light.

31. The method of claim 29, wherein the average intensity level of fluorescence from the tissue is at least fifty times greater that than the intensity of Raman shift emissions from the tissue.

32. The method of claim 21, further comprising gathering normalization data and using the normalization data with the measurements of the first scattered light and the measurements of the second scattered light to calculate a concentration of the chemical in the tissue.

33. The method of claim 21, wherein the light sensors are photomultiplier tubes.

* * * * *

UNITED STATES PATENT AND TRADEMARK OFFICE
CERTIFICATE OF CORRECTION

PATENT NO. : 7,558,619 B2
APPLICATION NO. : 11/244434
DATED : July 7, 2009
INVENTOR(S) : Scott Ferguson et al.

It is certified that error appears in the above-identified patent and that said Letters Patent is hereby corrected as shown below:

SPECIFICATION

Figure 16:
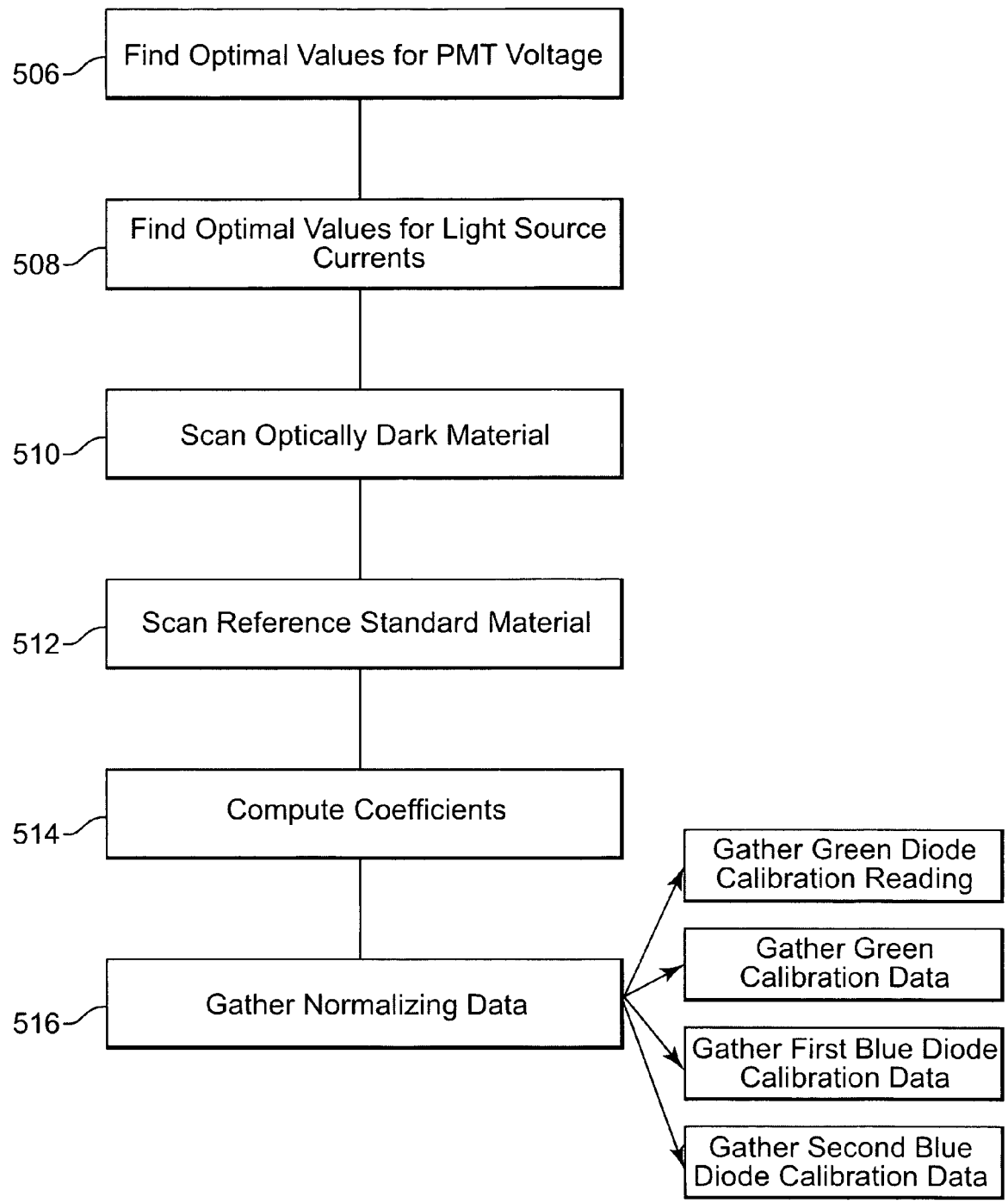
FIG. 16 is a flow chart of the field calibration process used with the apparatus.

| Column | Line | PTO | Should Read |
|---|---|---|---|
| 12 | 38 | "These materials" | -- The calibration process sets up components to their proper operating parameters and gathers data used to analyze and normalize raw data to compute the final measure of quantities of chemicals, for example carotenoids (or other selected molecules). This final measure may be referred to as the Carotenoid Score. The Carotenoid Score may be on any suitable range and reflects the level of carotenoids in the tissue. A suitable range may be 0 to 100,000. As shown in Figure 16, the calibration process may include: (1) finding optimal values for the voltage supplied to the PMTs and current supplied to the light sources, shown at blocks 506 and 508; (2) measuring an optically dark material for use in a "Dark Subtract" process, shown at block 510; (3) measuring a reference standard material that produces a Raman signal at a |

Signed and Sealed this

Twenty-second Day of June, 2010

David J. Kappos
*Director of the United States Patent and Trademark Office* shifted emission wavelength corresponding to that of carotenoids (thus for a light source of approximately 473 nanometers, a Raman signal of approximately 509 nanometers), shown at block 512; (4) computing coefficients of a linear equation for use in the data analysis to convert readings into Carotenoid Scores, shown at block 514; and (5) gathering data for normalization in Data Analysis, shown at block 516. Not all of these steps will be performed at once and they may be performed in a different order than shown. Reference standard materials are prepared samples that are designed for use in a calibration process. These materials --

| | | | |
|---|---|---|---|
| 15 | 33 | "Rarnan emission" | -- Raman emission -- |

CLAIMS

| Column | Line | PTO | Should Read |
|---|---|---|---|
| 24 | 2 | "developing at least" | -- developing for at least -- |
| 24 | 6 | "developing at least" | -- developing for at least -- |
| 24 | 27 | "computing the ratios" | -- computing sample value ratios -- |
| 24 | 28 | "from the resulting computed ratios" | -- from resulting computed sample value ratios -- |
| 24 | 29 | "extrapolating by" | -- interpolating by -- |
| 24 | 30 | "through the points" | -- through points -- |
| 24 | 31 | "from the" | -- from -- |

| | | | |
|---|---|---|---|
| 25 | 20 | "sampled is a wavelength range range" | -- sampled is a wavelength range -- |
| 25 | 34 | "first reflected light" | -- first scattered light -- |
| 25 | 35 | "first reflected light" | -- first scattered light -- |
| 25 | 46 | "second reflected light" | -- second scattered light -- |
| 25 | 48 | "light source measuring" | -- light sensor measuring -- |
| 25 | 52 | "light sensors, and" | -- light sensor, and -- |
| 25 | 54 | "light source; and" | -- light sensor; and -- |
| 26 | 30 | "the measurements from" | -- the measurement from -- |

UNITED STATES PATENT AND TRADEMARK OFFICE
CERTIFICATE OF CORRECTION

PATENT NO. : 7,558,619 B2 Page 1 of 1
APPLICATION NO. : 11/244434
DATED : July 7, 2009
INVENTOR(S) : Scott Ferguson et al.

It is certified that error appears in the above-identified patent and that said Letters Patent is hereby corrected as shown below:

CLAIMS

| Column | Line | PTO | Should Read |
|---|---|---|---|
| 24 | 24 | "method of claim 1 wherein" | -- method of claim 2 wherein -- |

Signed and Sealed this

Thirteenth Day of July, 2010

David J. Kappos
*Director of the United States Patent and Trademark Office*